United States Patent
Russak

(10) Patent No.: US 12,320,742 B2
(45) Date of Patent: Jun. 3, 2025

(54) MULTI-TEST KIT

(71) Applicant: INFINIPLEX LTD, Ra'anana (IL)

(72) Inventor: Ze'ev Russak, Netanya (IL)

(73) Assignee: INFINIPLEX LTD., Ra'anana (IL)

( * ) Notice: Subject to any disclaimer, the term of this patent is extended or adjusted under 35 U.S.C. 154(b) by 427 days.

(21) Appl. No.: 17/422,348

(22) PCT Filed: Dec. 31, 2019

(86) PCT No.: PCT/IB2019/061468
§ 371 (c)(1),
(2) Date: Jul. 12, 2021

(87) PCT Pub. No.: WO2020/148593
PCT Pub. Date: Jul. 23, 2020

(65) Prior Publication Data
US 2022/0120671 A1    Apr. 21, 2022

Related U.S. Application Data

(60) Provisional application No. 62/791,950, filed on Jan. 14, 2019.

(51) Int. Cl.
| G01N 21/25 | (2006.01) |
| G01N 21/03 | (2006.01) |
| G01N 21/77 | (2006.01) |

(52) U.S. Cl.
CPC ........... *G01N 21/253* (2013.01); *G01N 21/03* (2013.01); *G01N 21/77* (2013.01); *G01N 2021/0325* (2013.01)

(58) Field of Classification Search
None
See application file for complete search history.

(56) References Cited

U.S. PATENT DOCUMENTS

| | | | |
|---|---|---|---|
| 9,151,763 B2 * | 10/2015 | Osterfeld | B01L 3/5085 |
| 10,991,096 B2 * | 4/2021 | Adiri | G06T 7/0012 |
| 2010/0203521 A1 | 8/2010 | Klapperich et al. | |
| 2014/0045729 A1 | 2/2014 | Jones et al. | |
| 2015/0301058 A1 | 10/2015 | Schettini et al. | |
| 2016/0121326 A1 | 5/2016 | Lebedev et al. | |
| 2016/0256870 A1 | 9/2016 | Ismagilov et al. | |
| 2018/0016624 A1 | 1/2018 | Yue et al. | |

FOREIGN PATENT DOCUMENTS

| WO | WO2009046227 A1 | 4/2009 |
| WO | 2016/025698 A1 | 2/2016 |
| WO | WO2018165354 A1 | 9/2018 |

OTHER PUBLICATIONS

International Search Report issued Apr. 27, 2020 in PCT/IB2019/061468 (2 pages).
Written Opinion issued Apr. 27, 2020 in PCT/IB2019/061468 (6 pages).
Huang et al., Multicolor Combinatorial Probe Coding for Real-Time PCR. PLoS ONE. Jan. 14, 2011;6(1):e16033 (10 pages).
Rajagopal et al., Significant Expansion of Real-Time PCR Multiplexing with Traditional Chemistries using Amplitude Modulation. Sci Rep. Jan. 31, 2019;9(1):1053.
Rice et al., Virtual Barcoding using LATE-PCR and Lights-On/Lights-Off probes: identification of nematode species in a closed-tube reaction. Mitochondrial DNA A DNA Mapp Seq Anal. 2016;27(2):1358-1363.
Eppstein et al., Improved Combinatorial Group Testing for Real-World Problem Sizes. SIAM Journal on Computing 2007;36(5):86-98.
Aldridge et al., Group Testing: An Information Theory Perspective. arXiv:1902.06002v3 [cs.IT] Aug. 17, 2020 (141 pages).
Office Action issued in related Canadian Patent Application No. 3126622 dated Jul. 20, 2023 (4 pages).
International Preliminary Report on Patentability issued in PCT/IB2019/061468 dated Jul. 31, 2020 (8 pages).
Notice of Intent to Grant issued by the EPO in European Patent Application No. 19909635.5 dated Sep. 12, 2024 (6 pages).
Specification as allowed in related EP 19909635.5 received with Notice of Intent to Grant, dated Sep. 12, 2024 (69 pages).

* cited by examiner

*Primary Examiner* — Blaine Lankford
(74) *Attorney, Agent, or Firm* — Michael A. Whittaker

(57) ABSTRACT

A prefabricated multi-test kit, the kit that comprises a plurality of reaction cells, each one of at least two of the reaction cells holding reagents of a respective, different set of at least two tests selected from a group consisting of a plurality of different tests, the tests being distributed among the reaction cells in a manner that leaves reagents of each different one of the tests of the group in a respective different sub-combination of the reaction cells, and allows any sub-combination of the reaction cells to be indicative of a sub-group comprising all positive tests of the group when each reaction cell of the sub-combination that is indicative of the sub-group, contains an at least one positive test and none of the remaining reaction cells contain a positive test.

17 Claims, 9 Drawing Sheets

| Group size: | _4_ | _3_ | _5_ | _7_ | _11_ | _13_ | Test No. |
|---|---|---|---|---|---|---|---|
| Reminder: | 2 | 0 | 0 | 3 | 9 | 10 | 23670 |
| | 2 | 0 | 0 | 3 | 9 | 7 | 32910 |
| | 2 | 0 | 0 | 3 | 7 | 10 | 50970 |
| | 2 | 0 | 0 | 3 | 7 | 7 | _150_ |
| | 2 | 0 | 0 | 5 | 9 | 10 | 15090 |
| | 2 | 0 | 0 | 5 | 9 | 7 | 24330 |
| | 2 | 0 | 0 | 5 | 7 | 10 | 42390 |
| | 2 | 0 | 0 | 5 | 7 | 7 | 51630 |
| | 3 | 0 | 0 | 3 | 9 | 10 | 8655 |
| | 3 | 0 | 0 | 3 | 9 | 7 | 17895 |
| | 3 | 0 | 0 | 3 | 7 | 10 | 35955 |
| | 3 | 0 | 0 | 3 | 7 | 7 | 45195 |
| | 3 | 0 | 0 | 5 | 9 | 10 | _75_ |
| | 3 | 0 | 0 | 5 | 9 | 7 | 9315 |
| | 3 | 0 | 0 | 5 | 7 | 10 | 27375 |
| | 3 | 0 | 0 | 5 | 7 | 7 | 36615 |

Fig. 5B

| GROUP | 1 | 2 | 3 | 4 | 5 |
|---|---|---|---|---|---|
| 1 | BZ |  | B | ACZ |  |
| 2 |  | AB | AC | B |  |

Fig. 6B

| Control | Digit Position group(s) | Test(s) | Value(s) in base |
|---|---|---|---|
| 1 | 1,2 | C | 00<u>2</u>10 |
| 2 | 1,3 | B | 12<u>1</u>20 |
| 3 | 1,4 | Z | 100<u>1</u>0 |
| 4 | 1,5 | A, C | 0<u>2</u>21<u>0</u>, 00<u>2</u>1<u>0</u> |
| 5 | 2,3 | A, Z | 0<u>22</u>10, 10<u>01</u>0 |
| 6 | 2,4 | B | 1<u>2</u>1<u>2</u>0 |
| 7 | 2,5 | C, Z | 0<u>0</u>21<u>0</u>, 1<u>0</u>01<u>0</u> |
| 8 | 3,4 | | |
| 9 | 3,5 | Z | 10<u>0</u>1<u>0</u> |
| 10 | 4,5 | | |

Fig. 6C

MULTI-TEST KIT

CROSS-REFERENCE TO RELATED APPLICATIONS

The present invention is filed under 35 U.S.C. § 371 as the United States national phase of International Application No. PCT/IB2019/061468, filed Dec. 31, 2019, which claims the benefit of U.S. Provisional Application No. 62/791,950, filed Jan. 14, 2019, each of which are hereby incorporated in their entirety including all tables, figures, and claims.

FIELD AND BACKGROUND OF THE INVENTION

The present invention is generally related to performing multiple tests on a single sample, and is more specifically, but not exclusively, related to a method and a prefabricated multi-test kit that allow a user to perform all tests of the kit in parallel, and for a method of manufacturing the multi-test kit.

Chemical tests, whether performed at a laboratory, at a point of care, or at another place, are an integral part of today's health care systems, veterinary care services, environmental protection agencies, etc.

Such chemical tests may include, for example, tests for the presence of specific DNA Sequences, specific proteins, specific antibodies, toxin traces, explosives traces, etc. The tests may be determined to be positive based on physical measurements such as, for example, fluorescence intensities, phosphorescence intensities, electric conductivity, electric capacitance, optical opacity of a cell that a test takes place in, etc., as known in the art.

For example, chemical diagnostic tests play a central role in many aspects of patient care, including disease-diagnosis, monitoring progression of therapy, as well as screening for health and infection conditions. Chemical diagnostic tests are especially useful, as they may pinpoint the exact cause of a particular clinical manifestation and thus help a physician make a diagnosis and then, prescribe the right therapy for the patient.

However, chemical diagnostic testing processes are often very tedious, time-consuming, cumbersome, and slow. This is because a number of different tests (say for the presence of different bacteria, viruses, and/or fungi in a sample taken from a human patient or from a sick farm animal) often have to be performed for a given symptom and usually, each of those tests is performed individually. Moreover, because laboratories are constantly updating and adding new tests that facilitate medical diagnosis—say for the presence of certain metabolites in a sample, physicians tend to use more and more tests for diagnosis.

Indeed, over the last few decades, the total number of clinical tests and the number of types of different tests available to physicians have grown exponentially. However, those tests are often not user friendly, and increase costs in an already heavily burdened health care system, especially when performed separately. Very often, such non-concurrent tests result in delays in the processing of test results at the laboratories, which delays often prevent accurate diagnosis.

Thus, in a growing number of cases, many tests may need to be performed on a specific sample, and due to their number, with currently used techniques, those tests may need to be run in a sequential fashion in which each test is carried out separately (i.e. either in a separate reaction cell, or not concurrently, and very often, during separate visits to the laboratory).

Thus, very often, testing slows down the entire process of patient or animal to care and treatment, the handling of environmental crises, the forensic investigation of crime scenes, etc., as known in the art.

SUMMARY OF THE INVENTION

According to one aspect of the present invention there is provided a prefabricated multi-test kit, the kit comprising: a plurality of reaction cells, each one of at least two of the reaction cells holding reagents of a respective, different set of at least two tests selected from a group consisting of a plurality of different tests, the tests being distributed among the reaction cells in a manner that leaves reagents of each different one of the tests of the group in a respective different sub-combination of the reaction cells, and allows any sub-combination of the reaction cells to be indicative of a sub-group comprising all positive tests of the group when each reaction cell of the sub-combination that is indicative of the sub-group, contains an at least one positive test and none of the remaining reaction cells contain a positive test.

According to a second aspect of the present invention there is provided a method of manufacturing a multi-test kit, the method comprising: providing a plurality of reaction cells, and distributing a group consisting of a plurality of tests among the reaction cells, by adding reagents of each different one of the tests to a respective different sub-combination of the reaction cells and leaving reagents of a different set of at least two of the tests of the group in each respective one of at least two of the reaction cells, in a manner that allows any sub-combination of the reaction cells to be indicative of a sub-group comprising all positive ones of the tests of the group when each reaction cell of the sub-combination that is indicative of the sub-group, contains at least one positive test and none of the remaining ones of the reaction cells contain a positive test.

According to a third aspect of the present invention there is provided a method of carrying out a plurality of tests using a multi-test kit, the method comprising: receiving data identifying for each respective one of the plurality of tests, all reaction cells of the multi-test kit that contain an at least one positive test when the respective one of the plurality of tests is positive, dividing a sample among a plurality of reaction cells of the multi-test kit, each one of at least two of the reaction cells of the kit holding reagents of a respective, different set of at least two tests selected from the plurality of tests, the tests being distributed among the reaction cells in a manner that leaves reagents of each different test of the plurality of tests in a respective different sub-combination of the reaction cells, and allows any sub-combination of the reaction cells to be indicative of a sub-group comprising all positive tests of the plurality of tests when each reaction cell of the sub-combination that is indicative of the sub-group, contains an at least one positive test and none of the remaining reaction cells contain a positive test, measuring a physical property over each cell of the reaction cells of the kit that holds reagents of an at least one of the tests, for each one of the reaction cells of the kit that holds reagents of at least one of the tests, determining whether the reaction cell contains an at least one positive test, based on the measuring, and based on the determining and using the received data, identifying a subgroup comprising all positive tests of the plurality of tests.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings:

FIG. 5B is a simplified diagram illustrating group size—cell number combinations of a specific example, according to an exemplary embodiment of the present invention.

FIG. 6B is a simplified diagram illustrating an exemplary data mapping of tests to cells, based on the third exemplary method of distributing tests, according to an exemplary embodiment of the present invention.

FIG. 6C is a simplified diagram illustrating an exemplary scenario of repairing data mapping of the third exemplary method of distributing tests, according to an exemplary embodiment of the present invention.

DESCRIPTION OF THE PREFERRED EMBODIMENTS

Figure 1:
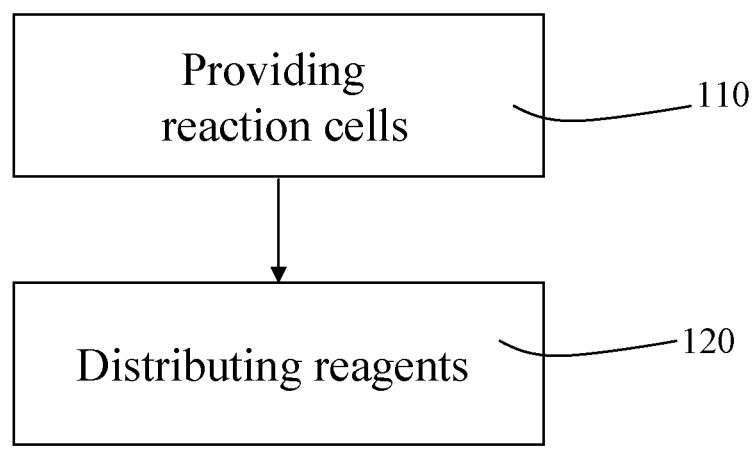
FIG. 1 is a simplified flowchart illustrating a first exemplary method of manufacturing a multi-test kit, according to an exemplary embodiment of the present invention.

The present embodiments comprise a multi-test kit, a method of manufacturing a multi-test kit, and a method of carrying out a plurality of tests using a multi-test kit.

As described in further detail hereinabove, in a growing number of cases, whether in a medical, environmental, or other field, many tests need to be performed on a specific sample, and due to their number, with hitherto used techniques, those tests would need to be run in an at least partially sequential fashion. Usually, each test indicates the presence (which makes the test positive) or absence (which makes the test negative) of a target element, such as a specific chemical compound, microorganism, antibody, DNA (Deoxyribonucleic acid) sequence, etc.

With currently used methods, each test has to be carried out separately (i.e. either in a separate reaction cell or not concurrently with other one of the tests).

A kit manufactured according to an exemplary method of the present invention, may be used for subjecting a sample (say a blood or other fluid sample taken from a human patient's or a farm animal's body, a sample taken from a contaminated water resource or a crime scene, etc.) to multiple test in parallel (i.e. without having to expose the sample to each test's reagents, separately).

More specifically, with a multi-test kit manufactured according to an exemplary method of the present invention, potentially, a sample may be subjected to a large number of tests in parallel, using a number of reaction cells that is significantly smaller than the number of tests.

The multi-test kit may be used by professional workers (say a nurse or a laboratory technician), by a patient herself, etc., as known in the art.

The kit's reaction cells may include, but are not limited to, for example, wells, vials, test tubes, etc., or any other element in which reagents of a mix used for a test may be deposited when manufacturing the multi-test kit, as described in further detail hereinbelow.

Thus, in an exemplary embodiment of the present invention, for manufacturing the multi-test kit, there is provided a plurality of reaction cells, be the cells wells, vials, test tubes, etc., or any combination thereof.

Each one of the kit's reaction cells is uniquely identifiable, say by a respective position (say the reaction cell's line and column positioning in the kit when made of several wells that are arranged in an array), by a respective marking (say a cell-specific label printed on a reaction cell such as a vial, or beside a reaction cell such as a well), etc., or any combination thereof.

Then, there are distributed a plurality of different tests among the provided plurality of reaction cells in a manner that leaves reagents of a different set of at least two tests selected from the plurality of different tests in each respective one of at least two of the provided reaction cells, as described in further detail hereinbelow.

The tests are distributed among the reaction cells, by adding each different one of the plurality of tests (i.e. by adding the test's reagents) to a respective different sub-combination of the reaction cells. That is to say that each one of the tests is to be performed using a different, though possibly partially overlapping, combination of reaction cells, as described in further detail hereinbelow.

The manner of distributing the tests among the kit's reaction cells, further allows any sub-combination of the provided reaction cells to be indicative of a sub-group of potentially positive tests. The sub-combination is indicative of the sub-group when each reaction cell of the sub-combination contains an at least one positive test and none of the remaining ones of the reaction cells contain a positive test, as described in further detail hereinbelow.

The sub-group of tests that the sub-combination of reaction cell is indicative of includes at least all positive tests of the group.

Optionally, the manner of distribution of the tests (i.e. of tests' regents) among the provided reaction cells further allows the sub-combination of the reaction cells to be indicative of all negative tests of the group. As a result, the sub-group of tests that the sub-combination of reaction cells is indicative of, contains all positive ones of the tests, and only the positive tests, as described in further detail hereinbelow.

Thus, in one example, all tests of the kit are mutually exclusive, say when the tests are for mutually exclusive mutations of a specific gene or peptide, and as a result, the sub-group includes all positive tests, and only the positive tests.

Optionally, the manner of distribution of the tests among the provided reaction cells further allows the sub-combination of the reaction cells to be indicative of all negative tests of the group, provided the number of concurrently positive tests is below a number predefined when manufacturing the kit. The number may be predefined, and indicated by a manufacturer of the kit (say on a manual or package of the kit), as described in further detail hereinbelow.

For example, a manufacturer (say the manufacturer's worker) may define the maximum number of concurrently positive tests to be two, in which case, the kit is accordingly manufactured so as to prevent any negative test from being identified as positive by inclusion in the sub-group of potentially positive tests, when two other tests are positive, as described in further detail hereinbelow.

Thus, in one example, all possible ambiguities possible when a number (say two) of the tests, which number is chosen by the manufacturer of the kit, are positive, are identified and dealt with by the manner in which tests are assigned to, and distributed among the reaction cells, as described in further detail hereinbelow. For example, the distributing may include adding one or more control reaction cells to the kit, so as to solve the ambiguities, as described in further detail hereinbelow.

Optionally, the manner of distribution of the reagents among the provided reaction cells further allows the sub-combination of the reaction cells to be indicative of all negative tests of the group, within an at least one degree of certainty predefined and indicated by the manufacturer of the kit, as described in further detail hereinbelow.

In one example, each degree of certainty informs a user of the kit on the probability that any test indicated as potentially positive (i.e. a test that belongs to the sub-group of tests that are potentially positive) is indeed positive, for a different number of concurrently positive tests, as described in further detail hereinbelow.

Thus, in one example, one degree of certainty informs a user on the probability that any test indicated as potentially positive, is indeed positive, when up to two tests may be concurrently positive. Further in the example, a second degree of certainty informs the user on the probability that any test indicated as potentially positive, is indeed positive, when up to three tests may be concurrently positive.

Optionally, a user of the kit is further provided with data that maps between each one of the plurality of tests and a respective sub-combination of the kit's reaction cells. The mapping identifies all reaction cells that contain an at least one positive test when the test mapped to the sub-combination is positive, as described in further detail to hereinbelow.

Thus, in one example, the kit includes a computer readable medium (say a Secure Digital (SD) card or a flash memory) that stores data that lists for each specific one of the tests, all reaction cells of the kit, that contain an at least one positive test when the specific test is positive.

Thus, potentially, a multi-test kit manufactured according to an exemplary method of the present invention, may be used for subjecting a single sample, say a one taken from a specific individual, to many tests in parallel—i.e. without having to expose the sample to each test (i.e. to the test's reagents) in a separately (say in a separate time frame) due to the size limits that such kits practically have.

The principles and operation of a multi-test kit, a method of manufacturing multi-test kit, and a method of using a multi-test kit, according to the present invention may be better understood with reference to the drawings and accompanying description.

Before explaining at least one embodiment of the invention in detail, it is to be understood that the invention is not limited in its application to the details of construction, and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1 which is a simplified flowchart illustrating a first exemplary method of manufacturing a multi-test kit, according to an exemplary embodiment of the present invention.

The kit may be used for subjecting a sample (say a blood or other fluid sample taken from a human patient's or farm animal's body, a sample taken from a contaminated water resource or from a crime scene, etc.) to multiple different tests in parallel (i.e. without having to expose the sample to each test separately (say in a different time frame), or use a second sample taken from the patient or animal for one or more of the tests).

The exemplary method of manufacture may by carried out, for example, by one or more industrial robots (say a warehouse robot or a molding robot), by one or more industrial machines, by a computer that controls the robot(s), the machine(s), etc., or any combination thereof, as described in further detail hereinbelow. The computer may include one computer, or rather two or more computers connected in a network, as known in the art.

For example, the method may be carried out by a computer that is programmed to carry out one or more of the method's steps 110-120 or one or more parts of the step 110-120—say by receiving input form a user (say a worker), by carrying out certain calculations, by controlling the robot(s) or machines(s), etc., as described in further detail hereinbelow.

The multi-test kit of the exemplary method of manufacturing is manufactured for a group of tests that exceeds the number of reaction cells to be included in the multi-test kit.

Potentially, with the kit manufactured according to the exemplary method, a sample may be subjected to a large number of different tests in parallel, even when the kit's number of reaction cells is significantly smaller than that large number of tests, as described in further detail hereinbelow.

In the first exemplary method of manufacturing, there are provided 110 a plurality of reaction cells, be the cells wells, vials, test tubes, etc., or any combination thereof, as described in further detail hereinbelow.

The provision 110 of the reaction cells may include using already manufactured reaction cells—say vials, test tubes, or plastic arrays of wells, taken from an existing inventory of such reaction cells, say by a warehouse robot or other machine in control by the computer.

Additionally or alternatively, the provision 110 of the reaction cells may include manufacturing the reaction cells themselves, through processes such as plastic molding, assembling of parts taken from an inventory to form an array or a collection of reaction cells, etc., say by a robot, a molding machine, another manufacturing machine, etc.

The multi-test kit is manufactured in a way that makes each one of the multi-test kit's reaction cells uniquely identifiable.

Optionally, each one of the kit's cells is uniquely identifiable by a respective position (say the reaction cell's line and column positioning in the multi-test kit when that kit is made of several wells that are arranged in a rectangular array), as described in further detail hereinbelow.

Additionally or alternatively, in order to make each one of the reaction cells uniquely identifiable, the provision 110 of the reaction cells further includes a cell-specific marking of each specific one of the kit's reaction cells—i.e. a one with which each specific one of the kit's cell is assigned a different number, color, or other identifier.

Thus, in some examples, as a part of the provisioning 110, a robot is instructed by the computer to print or affix a cell-specific label on each respective one of the kit's reaction cells (say vials or tubes), to print such a cell-specific label beside the reaction cell (say well), etc., or any combination thereof, as known in the art.

Next, the different tests are distributed 120 among the provided 110 plurality of reaction cells, using one or more of the methods of distributing 120 described in further detail hereinbelow. The tests may be distributed 120 by the computer, say using an industrial liquid handling robot that operates under control of the computer, for dispensing each test's reagents to specific cells that are selected by the computer, as described in further detail hereinbelow.

The tests are distributed 120 in a manner that leaves reagents of a different set of two or more of the tests in each respective one of at least two of the provided 110 reaction cells, as described in further detail hereinbelow. As a result, at least some of the reaction cells provided 110 in the kit, hold a mix of reagents that belong to a set of two or more different tests.

Each different one of the tests is distributed 120 among the provided 110 reaction cells, by adding reagents of the test to a respective different sub-combination of the provided 110 reaction cells. That is to say that each one of the tests is to be performed using a different though possibly, partially overlapping combination of reaction cells, as described in further detail hereinbelow.

Thus, in one example, the example featuring a kit that includes sixteen reaction cells that are marked $1^{st}$ to $16^{th}$, respectively, a first one of the tests may be distributed 120 by adding the first test's reagents to the $2^{nd}$, $3^{rd}$, $5^{th}$, $9^{th}$ and $12^{th}$ reaction cells, while a second one of the tests may be distributed 120 by adding the second test's reagents to the $2^{nd}$, $4^{th}$, $5^{th}$, $11^{th}$ and $16^{th}$ reaction cells, respectively.

The manner of distributing 120 the tests among the kit's reaction cells, further allows any sub-combination of the provided 110 reaction cells to be indicative of a sub-group of potentially positive tests, as described in further detail hereinbelow.

The sub-combination of reaction cells is indicative of the sub-group of potentially positive tests when each reaction cell of the sub-combination is positive—i.e. contains at least one positive test, and none of the remaining reaction cells provided 110 in the kit contain a positive test.

A determining as to whether each specific one of the cells is positive may be made, for example, according to a temperature or fluorescence measurement taken over each specific one of the cells that holds reagents of one or more tests, as described in further detail hereinbelow.

The sub-group of tests includes at least all positive tests of the group, as described in further detail hereinbelow.

Optionally, the manner of distributing 120 the tests among the provided 110 reaction cells further allows the sub-combination of the reaction cells to be indicative of all negative tests of the group. As a result, not only does the sub-group of tests that the sub-combination of reaction cells is indicative of, contain all positive ones of the kit's tests, but the sub-group also contains only the positive tests, as described in further detail hereinbelow.

Thus, in one example, all tests of the kit are mutually exclusive, say tests for mutually exclusive mutations of a specific gene or peptide, and as a result, the sub-group of tests includes all positive tests, and only the positive tests.

Optionally, the manner of distribution 120 of the tests among the provided 110 reaction cells further allows the sub-combination of the reaction cells to be indicative of all negative tests of the group, provided the number of concurrently positive tests is below a number predefined when manufacturing the kit. The number may be predefined, and indicated, for example, by a manufacturer of the kit (say on a manual or package of the kit), as described in further detail hereinbelow.

Thus, in one example, all possible ambiguities possible when a number (say two) of the tests, which number is predefined by the manufacturer of the kit, are positive, are identified and dealt with by the distributing 120 of the reagents among the provided 110 reaction cells, say using control cells, as described in further detail hereinbelow.

Optionally, the manner of distribution 120 of the tests among the provided 110 reaction cells further allows the sub-combination of the reaction cells to be indicative of all negative tests of the group of tests that the kit of manufactured for, within at least one degree of certainty. The degree of certainty may be predefined or calculated when manufacturing the kit, say as a part of one of the distribution 120 methods, as described in further detail hereinbelow.

In one example, as a part of the distributing 120, each degree of certainty is also indicated to a user of the kit, say on a paper label that may be printed (say by the computer) on a package of the kit or on a manual provided with the kit, as described in further detail hereinbelow. The degree of certainty informs the user of the kit on the probability that any test indicated as positive (i.e. a test that belongs to the sub-group that includes the potentially positive tests) is indeed positive, for a different number of concurrently positive tests.

Thus, in one example, one degree of certainty informs a user of the kit on the probability that any test indicated as positive, is indeed positive, when up to two tests may be concurrently positive. Further in the example, a second degree of certainty informs the user on the probability that any test indicated as positive, is indeed positive, when up to three tests may be concurrently positive.

Optionally, the exemplary manufacturing method further includes a step of providing mapping data.

The mapping data maps between each one of the different tests of the group and a respective sub-combination of reaction cells provided 110 in the kit.

The mapping data may be provided with the kit (say on a printed label affixed to the kit or on a manual provided with the kit), or rather be provided later, say when a buyer of the kit retrieves the data from a server used by the kit's manufacturer, as described in further detail hereinbelow.

Thus, for example, the method may include affixing a label bearing the mapping data to one of the kit's parts or rather, storing the mapping data on a computer readable medium (say an SD card) added to the kit, etc.

In one example, the kit includes computer readable medium (say an SD (Secure Digital) card or a flash memory), and the method includes storing the mapping data on the computer readable medium.

Optionally, the method rather includes transmitting the mapping data to a computer in use by a user of the multi-test kit upon request (say after buying the kit), say to an application installed on the user's computer, as described in further detail hereinbelow.

Thus, in one example, each kit is assigned a kit-specific key or rather a key that is specific to a group (say a batch) of kits that have a very same distribution 110 of test reagents, as described in further detail hereinbelow. In the example, the user has to use the key, for retrieving the mapping data from the manufacturer's remote server computer, say using the application installed on the user's computer.

The mapping data maps the test to the sub-combination, by identifying all provided 110 reaction cells that contain at least one positive test (and are thus positive cells) when the test mapped to the sub-combination is positive, as described in further detail hereinbelow.

Thus, when the specific one of the tests is positive, each one of the provided 110 reaction cells that the mapping data maps to that specific test, holds an at least one positive test.

The mapping data thus allows a user of the kit (or a computer—say a one implemented on the kit) to identify the sub-group that includes all positive ones of the tests (and potentially, only the positive cells), when a sub-combination that includes all reaction cells that have an at least one positive test is identified.

The cells that have an at least one positive test may be identified (i.e. the positive cells), say based on measurements of a certain physical property (say temperature or fluorescence) over each one of the kit's reaction cells that holds test reagents. That is to say that a determining as to whether the cell is positive or negative may be based on measuring of that physical property, as described in further detail hereinbelow.

Figure 2:
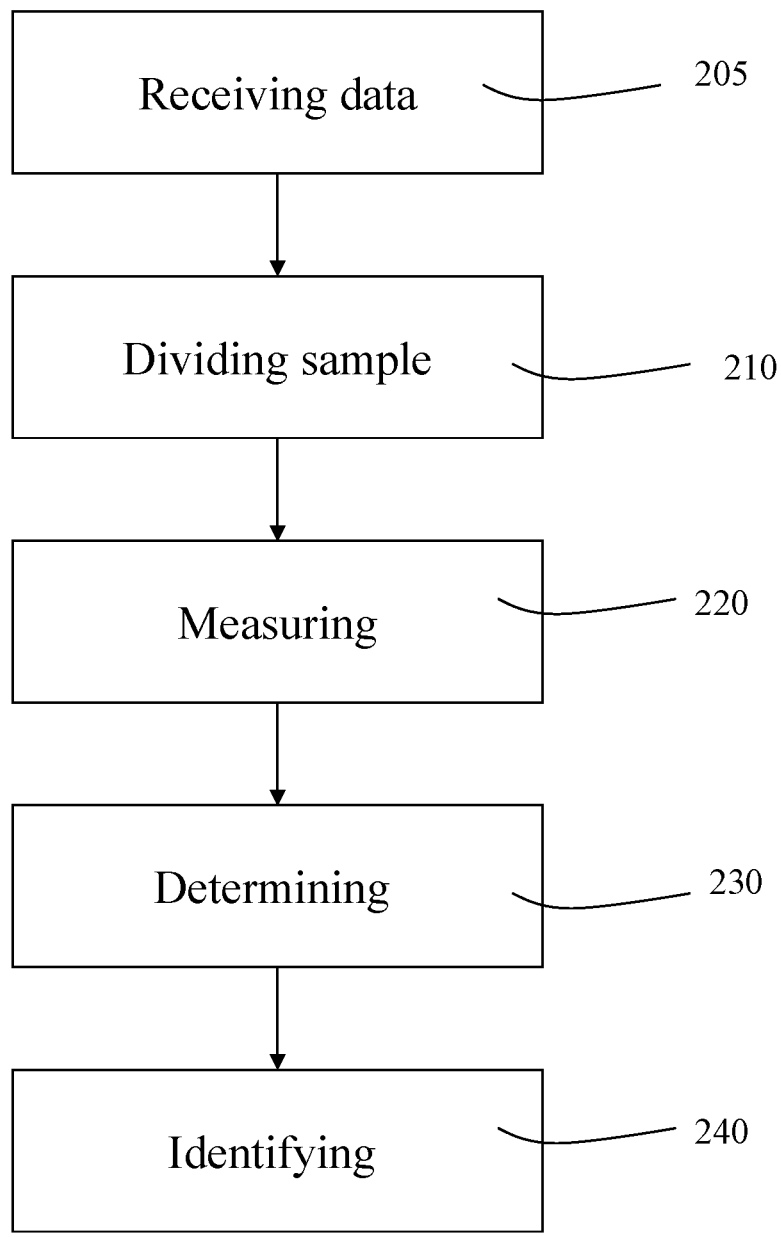
FIG. 2 is a simplified flowchart illustrating a first exemplary method of carrying out a plurality of tests using a multi-test kit, according to an exemplary embodiment of the present invention.

Reference is now made to FIG. 2 which is a simplified flowchart illustrating a first exemplary method of carrying out a plurality of tests using a multi-test kit, according to an exemplary embodiment of the present invention.

A first exemplary method of carrying out a plurality of tests, according to an exemplary embodiment of the present invention, is carried out using a multi-test kit—say the multi-test kit described in further detail and illustrated using FIG. 3 hereinbelow.

The first exemplary method of carrying the tests may include a step of receiving 205 mapping data that identifies for each respective one of the plurality of tests, all reaction cells of the multi-test kit that contain at least one positive test when the respective one of the plurality of tests is positive.

The received 205 mapping data thus maps each one of the tests to a respective sub-combination of cells, which sub-combination includes all cells that are positive (i.e. contain at least one positive test) when the test is positive, as described in further detail hereinbelow.

Thus, when the specific one of the tests is positive, each one of the kit's reaction cells of the list mapped to that specific test, holds an at least one positive test.

The mapping data thus provides for identifying the sub-group that includes all positive ones of the tests (and potentially, only the positive cells), when a sub-combination that includes all reaction cells that have an at least one positive test is identified by the user, as described in further detail hereinabove.

The mapping data may be received 205 before subjecting a sample to the tests (say before carrying out the steps of dividing 210, measuring 220, and determining 230, as described in further detail hereinbelow), or rather later (say after one or more of steps 210-230), as described in further detail hereinbelow.

Optionally, the mapping data is provided 205 with the kit, say on a printed label affixed to the kit, on a manual provided with the kit, on a computer readable memory included in the kit, etc., as described in further detail hereinabove.

Additionally or alternatively, the mapping data may rather be received 205 later (say after a user receives the kit), say by a computer application that runs on a computer processor installed on the kit, or rather by an application that is downloaded to a computer in use by a user of the kit. In one example, the application retrieves 205 the mapping data from a server in use by the kit's manufacturer, as described in further detail hereinabove.

The exemplary method of carrying out the plurality of tests using the multi-test kit further includes a step of dividing 210 a sample among a plurality of reaction cells of the multi-test kit.

Each one of at least two of the reaction cells of the kit holds reagents of a respective, different set of at least two tests selected from the plurality of tests. Further, the tests are distributed among the reaction cells in a manner that leaves reagents of each different test of the plurality of tests in a respective different sub-combination of the reaction cells, as described in further detail hereinbelow.

The manner in which the tests are distributed among the reaction cells, allows any sub-combination of the reaction cells to be indicative of a sub-group that comprises all positive tests of the plurality of tests when each reaction cell of the sub-combination contains an at least one positive test and none of the remaining reaction cells contain a positive test, as described in further detail hereinbelow.

Next in the exemplary method of carrying out the plurality of tests, there is measured 220 a physical property over each specific one of the reaction cells of the kit that contains reagents of one or more of the test.

The physical property may be measured 220, for example, using one or more sensors installed on the kit and by a computer that is connected to the sensors, as described in further detail hereinbelow. The sensors (say thermometers or photometers) may present the measurements 220 to a user of the kit, or rather be sampled, for reading the measurements 220, say by a computer, as described in further detail hereinbelow.

Thus, in one example, the multi-test kit includes one or more sensors that measure 220 the physical property over each specific one of the kit's reaction cells, say a thermometer, photometer, etc., as described in further detail hereinbelow.

In the example, the kit further includes a computer that is connected to the sensors and that reads and processes the measurements 220 taken by the sensors, say a computer that includes a computer processor, a memory, a circuit and a small LCD or other screen—that are installed on the kit, as known in the art.

In a second example, the kit includes an interface with a socket (say a USB socket) that allows a user to connect his computer to the kit, for reading the measurements 220 taken by the sensors.

Next in the exemplary method, for each one of the reaction cells of the kit, there is determined 230 whether the reaction cell contains at least one positive test (and is thus a positive cell), based on that measuring 220.

The reaction cell is thus determined to be positive based on that measuring 220, without determining 230 yet exactly which one (or more) of the specific reaction cell's tests (i.e. the tests that reagents thereof are held in the positive reaction cell) is indeed, positive.

Thus, in one example, the kit's computer or rather the user's computer determines 230 for each one of the kit's cells, if the cell holds an at least one positive test based on the processing of the measurements 220 taken by the sensors.

Optionally, the computer (whether the kit's or the user's) indicates which cell(s) are determined 230 to hold an at least one positive test, to the user, say on a small LCD (Liquid Crystal Display) screen that may be built into the kit, on a screen of a computer in wireless communication with the kit's computer, etc., as described in further detail hereinbelow.

Finally, based on the determining 230 and using the received 205 data, a subgroup that comprises all positive tests of the plurality of different tests is identified 240, say by the kit's computer or by the user's computer connected to the kit, as described in further detail hereinbelow.

Optionally, the manner of distribution of the tests among the reaction cells further allows the sub-combination of the reaction cells to be indicative of all negative tests of the plurality of tests. Accordingly, the method further comprises identifying 240 all negative tests of the plurality of tests, based on the determining 230 and using the received 205 data, as described in further detail hereinbelow.

Optionally, the manner of distribution of the tests among the reaction cells further allows the sub-combination of the reaction cells to be indicative of all negative tests of the plurality of tests, provided the number of concurrently positive tests is below a predefined number (say a number defined when manufacturing the kit). In which case, the method further comprises identifying 240 all negative tests of the plurality of tests, based on the determining 230 and using the received 205 data, provided the number of concurrently positive tests is indeed, below the predefined number, as described in further detail hereinbelow.

Optionally, the manner of distribution of the tests among the reaction cells further allows the sub-combination of the reaction cells to be indicative of all negative tests of the plurality of tests, within a predefined degree of certainty. Accordingly, the method further comprises identifying 240 all negative tests of the plurality of tests, within the predefined degree of certainty, based on the determining 230 and using the received 205 data, as described in further detail hereinbelow.

Figure 3:
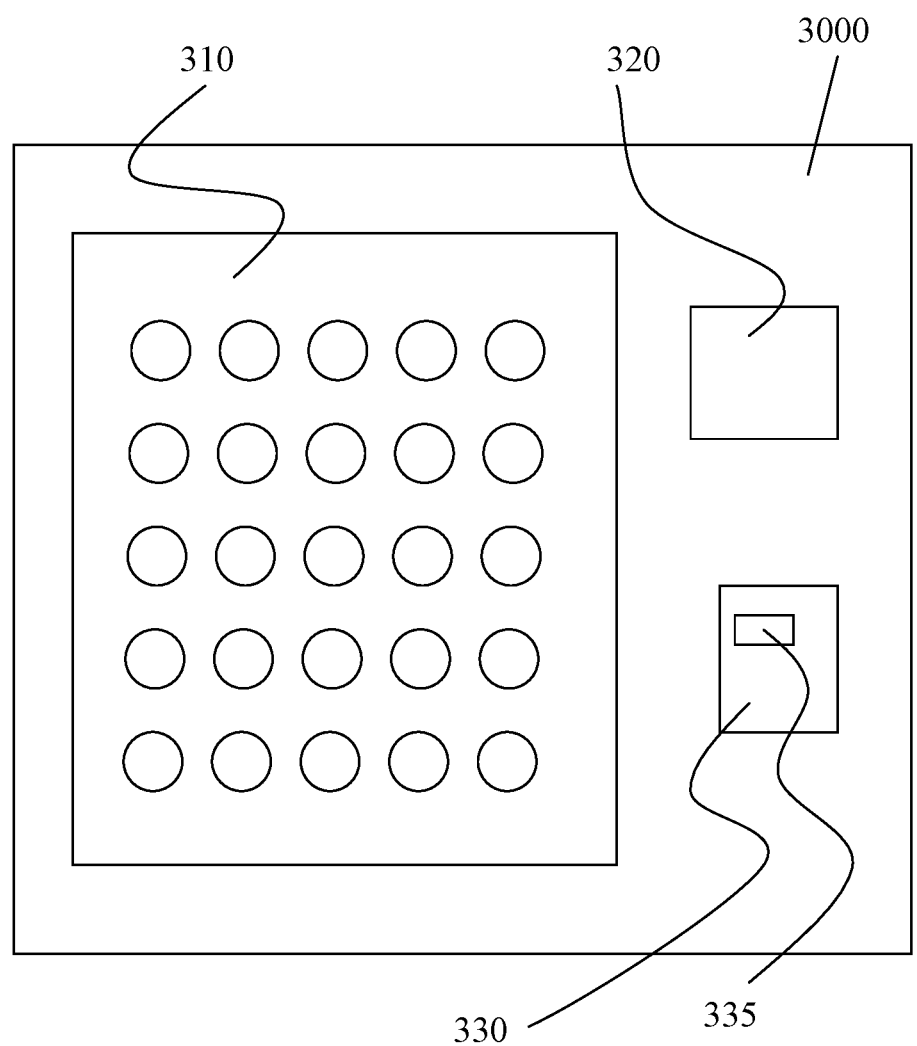
FIG. 3 is a simplified block diagram illustrating a first exemplary prefabricated multi-test kit, according to an exemplary embodiment of the present invention.

Reference is now made to FIG. 3 which is a simplified block diagram illustrating a first exemplary prefabricated multi-test kit, according to an exemplary embodiment of the present invention.

A multi-test kit 3000 prefabricated according to an exemplary embodiment of the present invention, say using the exemplary manufacturing method illustrated using FIG. 1 hereinabove, includes a plurality of reaction cells 310. The reaction cells 310 may include, for example, two or more wells that may be arranged in an array as illustrated in FIG. 3, two or more test tubes, vials or other containers, etc., or any combination of elements that can contain test reagents, as known in the art.

Each one of at least two of the reaction cells 310 holds reagents of a respective, different set of at least two tests. The two tests are selected from a group that includes a plurality of different tests, as described in further detail hereinabove.

The multi-test kit 3000 is manufactured in a way that makes each one of the multi-test kit's 3000 reaction cells 310 uniquely identifiable, as described in further detail hereinabove, and as illustrated using FIG. 1.

Optionally, each one of the kit's reaction cells 310 is uniquely identifiable by virtue of the cell's respective position (say the reaction cell's line and column positioning in the kit 3000 when the kit's 3000 reaction cells 310 include a plurality of wells 310 that are arranged in a rectangular array, as illustrated in FIG. 3)

Additionally or alternatively, each one of the reaction cells 310 is uniquely identifiable by virtue of a cell-specific marking of each one of the kit's 3000 reaction cells 310. For example, the cells 310 may be identifiable using a different cell-specific label that is affixed to or printed on, each respective one of the kit's 3000 reaction cells (say vials or tubes) 310, printed beside the reaction cell (say well) 310, etc., or any combination thereof, as described in further detail hereinabove.

The tests are distributed among the kit's 3000 reaction cells 310, by adding reagents of each different one of the plurality of tests to a respective different sub-combination of the reaction cells 310, as described in further detail hereinbelow. Thus, the tests are distributed among the kit's 3000 reaction cells 310 in a manner that leaves reagents of each different one of the tests in a respective different sub-combination of the reaction cells 310.

That is to say that each one of the tests is to be performed using a different, though possibly partially overlapping, combination of reaction cells 310, as described in further detail hereinbelow.

Thus, in one example, the example featuring a kit 3000 that includes twenty five reaction cells that are marked $1^{st}$ to $25^{th}$, respectively, a first one of the tests may be distributed by adding the first test's reagents to the $2^{nd}$, $3^{rd}$, $5^{th}$, $12^{th}$, $17^{th}$, $19^{th}$ and $24^{th}$ reaction cells, while a second one of the tests may be distributed by adding the second test's reagents to the $1^{st}$, $3^{rd}$, $9^{th}$, $12^{th}$, $18^{th}$, $19^{th}$ and $21^{st}$ reaction cells, respectively.

The tests are distributed among the kit's 3000 reaction cells 310 in a manner that allows any sub-combination of the reaction cells 310 to be indicative of a sub-group that comprises all positive tests of the group. The sub-combination of the cells 310 is indicative of that sub-group of tests, when each reaction cell 310 of the sub-combination contains an at least one positive test and none of the remaining reaction cells 310 contain a positive test, as described in further detail hereinabove.

The manner of distribution thus provides for identifying a sub-group that includes all positive ones of the tests (and potentially, only positive tests), based on the sub-combination that includes all positive reaction cells (i.e. each one of the cells 310 that holds at least one positive test), as described in further detail hereinabove.

Optionally, the manner in which the tests are distribution among the reaction cells 310 further allows the sub-combination of the reaction cells 310 to be indicative of all negative tests of the group that the kit 3000 is manufactured for, as described in further detail hereinabove. As a result, not only does the sub-group of tests that the sub-combination of reaction cells 310 is indicative of, contain all positive ones of the multi-test kit's 3000 tests (i.e. the group's different tests), but the sub-group also contains only the positive ones of the group of tests, as described in further detail hereinabove.

Optionally, the sub-combination of the reaction cells 310 is further indicative of all negative tests of the group, provided the number of concurrently positive tests is below a number predefined and indicated, say by a manufacturer of the kit 3000, as described in further detail hereinabove.

Optionally, the manner of distribution of the tests among the reaction cells 310 further allows the sub-combination of the reaction cells 310 to be indicative of all negative tests of the group, within at least one degree of certainty. The degree(s) of certainty may be predefined, calculated, or indicated, for example, by the manufacturer of the kit 3000, as described in further detail hereinabove.

Optionally, the kit 3000 further includes a computer readable memory (say portable flash memory, an SD Card, etc., as known in the art) 320 or rather a printed label or document that bears mapping data. The mapping data maps between each one of the different tests of the group and a respective sub-combination of cells 310, (i.e. to some of the kit's 3000 reaction cells 310), as described in further detail hereinbelow.

The mapping data maps between the tests and cells 310, for example, by identifying for each specific one of the tests, which ones of the kit's 3000 reaction cells 310 contain at least one positive test when the specific test is positive, as described in further detail hereinabove.

In one example, the mapping data is arranged in a table, say in a table stored on the computer readable memory 320 or printed on the label or document.

In the example, each one of the table's rows identifies the test that the row pertains to (say in a field positioned in a first column of the table, in that row) and lists all cells 310 they hold an at least one positive test when the test that the row pertains to is positive (say in the row's other fields).

Optionally, the mapping data that maps between the tests and cells 310 is rather transmitted to a computer in use by a user of the kit upon request (say after the user buys the kit), say to an application that the user has to download and install on the user's computer, as described in further detail hereinabove.

Thus, in one example, each kit 3000 is assigned a kit-specific key or rather a key that is specific to a group (say a batch) of kits that have a very same distribution of reagents, as described in further detail hereinabove.

In the example, the user has to use the key, for retrieving the mapping data from the manufacturer's remote server computer, say using the application installed on the user's computer.

The data that maps between the tests and reaction cells 310 allows a user of the kit 3000 to identify the sub-group that includes all positive ones of the tests (and potentially, only the positive cells), when a sub-combination that includes all reaction cells 310 that have an at least one positive test is identified by the user, as described in further detail hereinabove.

The user may determine which ones of the reaction cells 310 hold an at least one positive test, say by observing or measuring a certain physical property over each specific one of the kit's 3000 reaction cells 310, say a specific change in a color state of the reagents inside the cell 310, as described in further detail hereinabove.

Optionally, the kit 3000 further includes one or more sensors that are configured to measure the physical property's value over each specific one of the kit's 3000 reaction cells 310, say a thermometer, photometer, etc., as known in the art.

In one example, each specific one of the reaction cells 310 is coupled to one or more of the sensors, and each sensor coupled to the specific cell is configured to measure the physical property's value over the specific cell, say by virtue of deployment inside or beside the specific cell 310.

In a first example, the kit 3000 further includes a computer 330 that is connected to, and is thus in communication with, the sensors. The computer 330 includes a computer processor, a computer memory, a circuit and a small LCD 335 or other screen—that are installed on the kit 3000, as known in the art.

The computer 330 is configured, say by programming, using an electric circuit, or both by programming and using an electric circuit, to read the physical property value measured by the sensors and to determine for each specific one of the cells 310, whether the cell holds at least one positive test, based on the physical property measured over the specific cell 310.

In a second example, the kit 3000 includes an at least partially physical interface—say a one with a USB or other socket, a computer processor that runs software based protocol components, etc., or any combination thereof, as known in the art. The interface is connectable to a computer that is external to the kit 3000, for allowing the external computer to read the physical property values measured by the sensors. Thus, a user may connect her computer to the kit, and use the computer for determining for each one of the cells 310, whether the cell holds at least one positive test, say using the mapping data, as described in further detail hereinbelow.

The computer (whether the kit's or the user's) may indicate which cell(s) 310 are determined to hold an at least one positive test, to the user, say on the small LCD (Liquid Crystal Display) screen 335, on a screen of a computer in communication with a computer of the kit 3000, etc.

Optionally, the computer (whether the user's or the kit's) further uses the mapping data, to identify a subgroup comprising all positive tests of the tests of the to group, based on the cell 310 determined to hold an at least one positive test, as described in further detail hereinabove.

In a third example, a user of the kit herself may determine the subgroup that comprises all positive tests of the tests of the group, based on the cells 310 determined to hold an at least one positive test, using the mapping data, as described in further detail hereinbelow.

Optionally, the user determines which kit's 3000 cells 310 hold an at least one positive test, by herself, say based on an indication provided by one or more of the sensors, such as a reading of a thermometer or a change in opacity of one of more of the cell's 310, as described in further detail hereinbelow.

Figure 4:
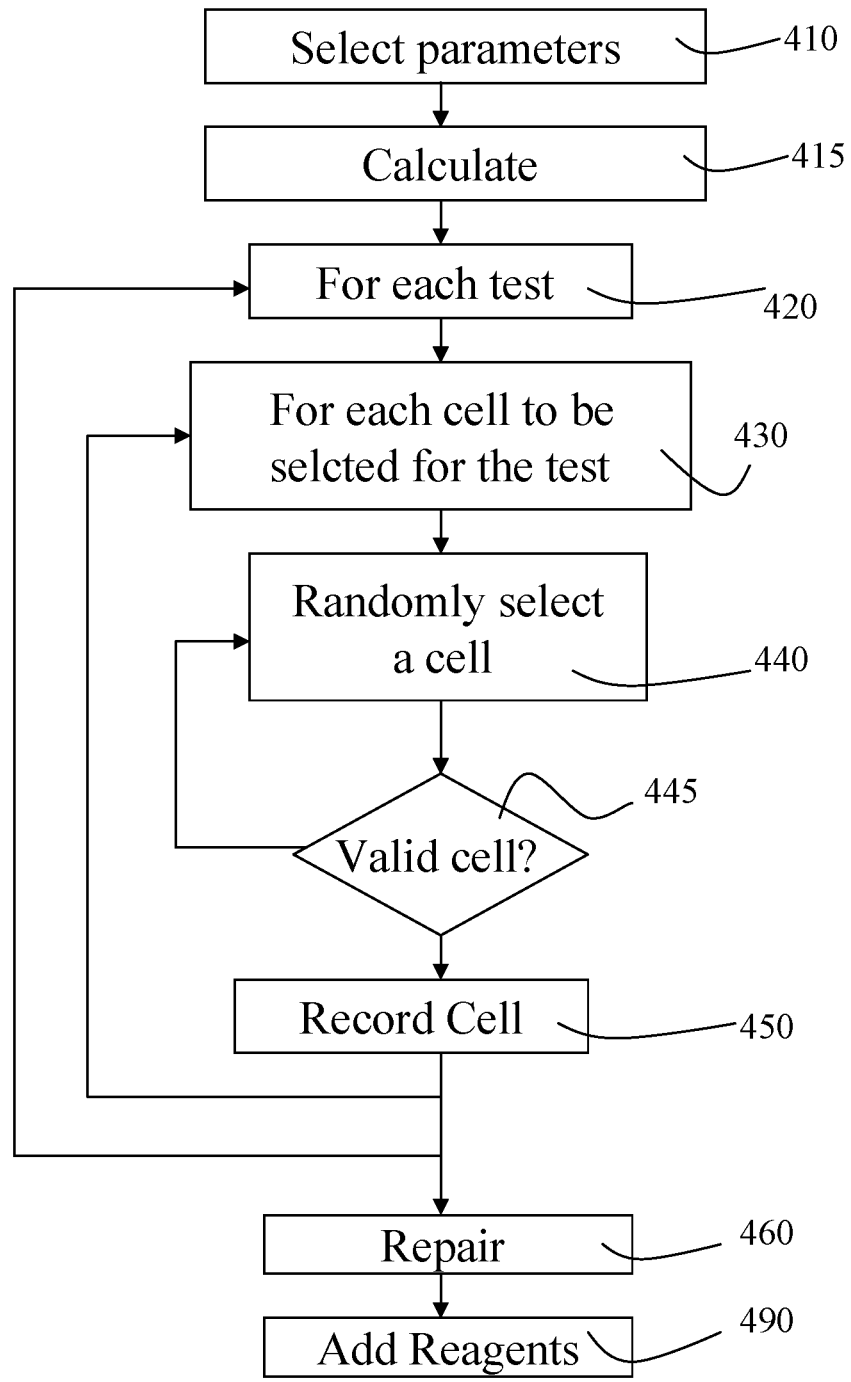
FIG. 4 is a simplified flowchart illustrating a first exemplary method of distributing tests in a multi-test kit, according to an exemplary embodiment of the present invention.

Reference is now made to FIG. 4, which is a simplified flowchart illustrating a first exemplary method of distributing tests in a multi-test kit, according to an exemplary embodiment of the present invention.

A first exemplary method of distributing tests in a multi-test kit, according to an exemplary embodiment of the present invention, may form at least a part of the multi-test kit manufacturing method, as described in further detail hereinabove, and as illustrated using FIG. 1.

The first exemplary distribution method is based on random numbers.

In the first method of distribution, a user selects (i.e. inputs) 410 the maximum number of tests that can be reliably executed in a same reaction cell (which number is also referred to hereinbelow as the maximum density), say using the computer that performs the manufacturing method, as described in further detail hereinabove.

Optionally, the user also selects 410 the maximum number of concurrently positive tests, as described in further detail hereinbelow.

Next, there is calculated 415 the number of reaction cells for the multi-test kit, and the number of cells that each test is distributed between, say by a computer, as described in further detail hereinabove.

In the exemplary method of distributing, when the user-input 410 number of concurrently positives tests (i.e. tests that may be both positive for a same sample) is denoted 'd', the number of different tests that the kit is manufactured for, is denoted 'n', and the number of reaction cells needed is denoted 't', t equals $2 \times \log n + 4 \times d \times \log(e \times n/d)$, rounded up to the next multiple of d.

Further in the exemplary first distribution method, the number of cells that each test is distributed between (by adding the test's reagents to each one of the cells that the test is distributed between) that is denoted hereinbelow as 'c' is equal to t/2d.

Thus, in one example, the multi-test kit is meant to be used, and is thus manufactured for 210 different tests, and a user (say a manufacturer's worker) inputs 410 a maximal number of concurrent positives that is 2. As a result, the number of reaction cells needed in the kit is given by $2 \times \log 210 + 4 \times 2 \times \log(e \times 210/2)$, rounded up to the next multiple of 2—i.e. 24 reaction cells.

Further in the example, each one of the tests (i.e. the test's reagents) is to be distributed between 24/(2×2) of the kit's reaction cells—i.e. between 6 reaction cells.

In the example, the kit is thus manufactured by providing 110 twenty four reaction cells, and distributing 120 each one of the tests, by adding 120 the test's reagents to each one of respective, randomly selected six of the twenty four cells, as described in further detail hereinabove.

For determining the specific reaction cells, for each test 420 to be distributed 120 between, the exemplary method of distribution iterates 430 c times, and in each iteration, the method randomly selects 440 another cell for the specific test's reagents to be added to. In each one of the c iterations 430, there is also verified 445 that the reaction cell selected 440 in the iteration, is still not selected for a number of tests that is greater than the maximum density.

Thus, in the above example, the exemplary method iterates 430 six times, and in each iteration, randomly selects 440 another cell for the specific test's reagents to be added to, while verifying 445 that the cell can be selected for the test without exceeding the maximum density, as described in further detail hereinabove. If the cell cannot be selected for the test without exceeding the maximum density, another cell is selected 440 randomly for the test.

The selected 440 cell is then recorded 450 as a part of the mapping data that identifies all the kit's reaction cells that contain an at least one positive test when the test thus mapped to those cells is positive, say on a computer memory, as described in further detail hereinabove. The mapping data thus maps between the test and the selected 440 cells, as described in further detail hereinabove.

However, a false positive (i.e. a negative test included in the sub-group that includes all positive tests) may still occur due to an overlap between a sub-combination of the reaction cells that the false positive is mapped to, and combined, sub-combinations of the reaction cells that two or more other tests are mapped to. The probability for such a false positive to occur when up to two tests can be concurrently positive is accordingly, predefined or calculated, say by a computer, to be: $2^{(-t/2d)}$.

Optionally, the probability may be reported to a user, say as a degree of certainty printed on a manual or a label, as described in further detail hereinabove.

In one example, each one of one or more degrees of certainty informs a user of the kit on the probability that any test indicated as positive (i.e. a test that belongs to the sub-group of tests that are potentially positive) is indeed positive, for a different number of concurrently positive tests.

Thus, in one example, one degree of certainty informs a user on the probability that any test indicated as positive, is indeed positive, when up to two tests may be concurrently positive. Further in the example, a second degree of certainty informs the user on the probability that any test indicated as positive, is indeed positive, when up to three tests may be concurrently positive.

Optionally, the exemplary method of distribution further includes a step of repairing 460.

In the step of repairing 460, the mapping data is analyzed by exhaustively iterating over all possible combinations of tests, so as to find any possible obscuring of a first test's result (whether positive or rather, negative) by the predefined number ('d') of concurrently positive other tests. In that exhaustive iteration, there are found all cells mapped by the mapping data to one or more tests of a specific combination of d tests, which mapped cells overlap with the cells mapped by the mapping data to the first test.

Then in the repairing 460, a new set of cells is selected for the first test, and the exhaustive iteration is performed again, so as to find any similar overlap (i.e. any obscuring left or introduced by the new set of cells).

The repairing 460 continues, by selecting a new set of cells for any test found to be mapped to cells overlapped by a combination of cells of other tests, and then exhaustively iterating again over all possible combinations of tests, so as to find any possible obscuring left and selecting a new set of cells for the obscured test, and so on and so forth, until no such obscuring can be found.

Thus, in a first example, four tests are denoted 'A', 'B', 'C', and 'D', respectively.

In the first example, Test A is distributed to reaction cells that are numbered 16, 4, 24, 6, 3, 10, respectively, and Test B is distributed to reaction cells that are numbered 1, 10, 15, 2, 13, 11, respectively. Further in the first example, Test C is distributed to reaction cells that are numbered 23, 5, 10, 18, 17, 14, respectively, and Test D is distributed to reaction cells that are numbered 2, 18, 13, 14, 17, 11, respectively.

In the first example, when carrying out the step of repairing 460, all possible combinations of two concurrently positive tests are found, and the cells mapped to any such two tests are checked for overlapping all cells mapped to a specific, other one of the tests.

Accordingly, in that step of repairing 460, the cells mapped to the combination of Tests A+B (i.e. to Test A, Test B, or both) are found to include cells number 16, 4, 24, 6, 3, 10, 1, 15, 2, 13, 11.

The cells mapped to the combination of Tests A+C (i.e. to Test A, Test C, or both) are found to include cells number 16, 4, 24, 6, 3, 10, 23, 5, 18, 17, 14, and the cells mapped to the combination of Tests A+D (i.e. to Test A, Test D, or both) are found to include cells number 16, 4, 24, 6, 3, 10, 2, 18, 13, 14, 17, 11.

Further in the example, the cells mapped to the combination of Tests B+C (i.e. to Test B, Test C, or both) are found to include cells number 1, 15, 2, 13, 11, 23, 5, 10, 18, 17, 14, and the cells mapped to the combination of Tests B+D (i.e. to Test B, Test D, or both) are found to include cells number 1, 10, 15, 2, 13, 11, 18, 14, 17.

Further, the cells mapped to the combination of Tests C+D (i.e. to Test C, Test D, or both) are found to include cells number 23, 5, 10, 18, 17, 2, 13, 14, 11.

Based on the above, an overlap is found between the cells mapped to the combination of Tests B+C and the cells mapped to Test D, since each one of the cells mapped to Test D (i.e. cells number 2, 18, 13, 14, 17, 11) is also included in the cells that either Tests B or Test C is mapped to.

That is to say that in the specific example, when both Test B and Test C are positive, each one of reaction cells number 1, 15, 2, 13, 11, 23, 5, 10, 18, 17, 14 is positive (i.e. contains one or more positive tests). However, the mapping data maps Test D too to cells number 2, 18, 13, 14, 17, 11, and as a result, Test D may be included in the sub-group of positive tests even when not positive, as described in further detail hereinabove.

In order to remove that ambiguity thus found in the mapping data, a new set of cells is selected (say randomly) for Test D, say a one that includes cells number 16, 13, 2, 14, 20, 24.

Then, the mapping data is updated accordingly and analyzed by exhaustively iterating over all possible combinations of tests, so as to find any such ambiguity if left, and repair the left ambiguity in a similar way, and so on and so forth, until no such ambiguity is found in the mapping data, as described in further detail hereinabove.

Alternatively, in the repairing 460, rather than selecting new cells for any test that may be a false positive when a combination of other ones of the tests is positive, the test may remain assigned to the cells already mapped to the test, but also to an additional one of the kit's cells.

Thus, in one example, the test that is identified as a potentially false positive, is further assigned and the mapped to a specific one of the kit's cells, by updating the mapping data accordingly, as described in further detail hereinbelow.

After the repairing 460, the reagents of each specific one of the tests are added 490 to each one of the kit's cells that the mapping data maps the specific test to, say by a robot, as described in further detail hereinbelow.

Figure 5A:
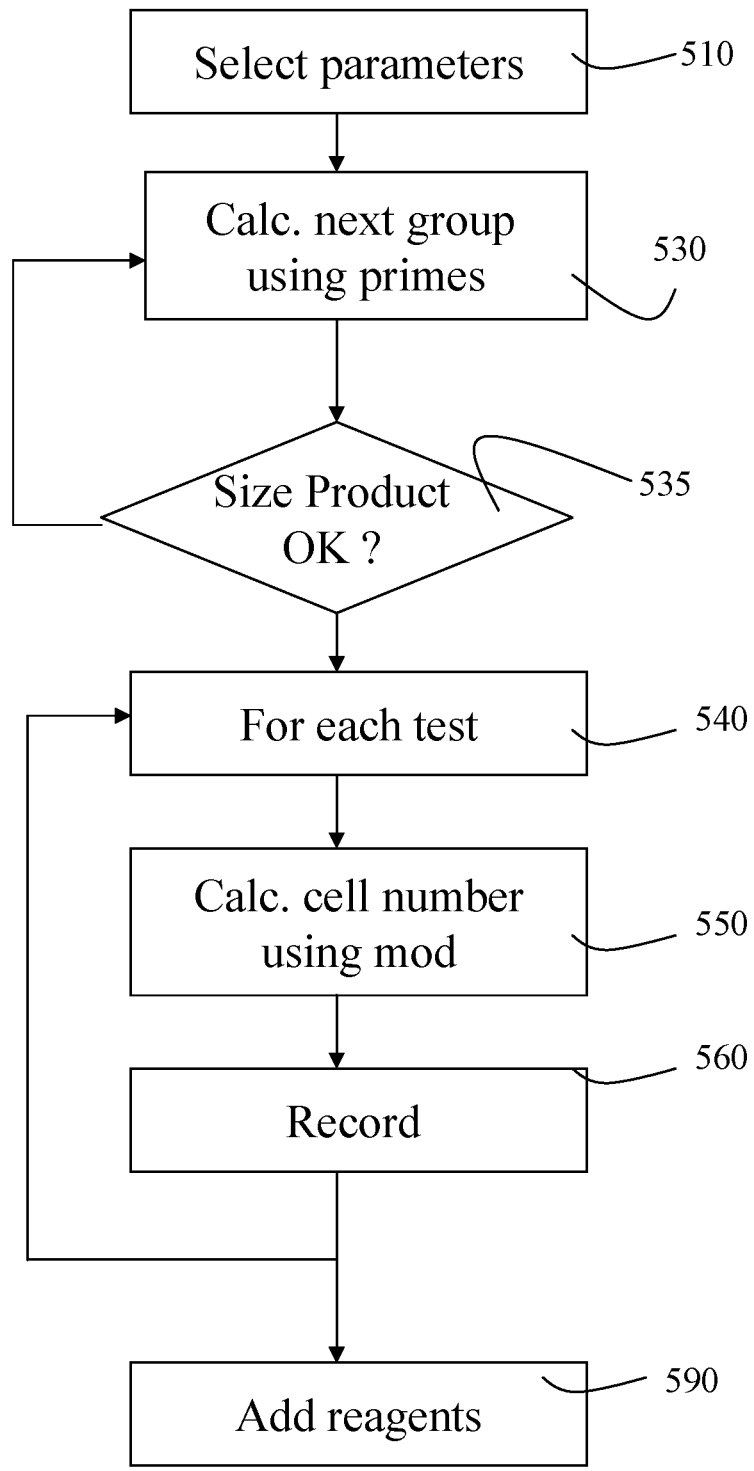
FIG. 5A is a simplified flowchart illustrating a second exemplary method of distributing tests in a multi-test kit, according to an exemplary embodiment of the present invention.

Reference is now made to FIG. 5A, which a simplified flowchart illustrating a second exemplary method of distributing tests in a multi-test kit, according to an exemplary embodiment of the present invention.

A second exemplary method of distributing tests in a multi-test kit, according to an exemplary embodiment of the present invention, may form at least a part of the multi-test kit manufacturing method, as described in further detail hereinabove, and as illustrated using FIG. 1.

The second exemplary distribution method is based on powers of prime numbers.

In the second exemplary method of distribution, a user (say a user of a manufacturing robot) is asked (say prompted on a computer screen of the robot) to select (i.e. input) 510 the number of tests and the maximum number of tests that can be reliably executed in a same reaction cell (also referred to hereinbelow as the maximum density).

Optionally, the user is also asked to select 510 the maximum number of tests that can be concurrently positive, as described in further detail hereinabove.

Next, there are calculated two or more cell groups.

Each group's size (i.e. the number of cells included in the group) is calculated 530 in turn, by raising a different but smallest one of the prime numbers (the prime numbers being 1, 2, 3, 5, 7, 11, 13, etc. as known in the art) in the power of the lowest natural number that makes the size no smaller than a minimal number of cells. The minimal number of cells is calculated by dividing the number of tests (i.e. the number of tests that the kit is meant to be used for and is thus manufactured for), by the user-input 510 maximum density.

Thus, for example, when the user-input number of tests is 210 and the user-input maximum density is 70, the minimal number of cells per group is 210/70=3.

A size of a first one of the cell groups cannot be the result of raising the number 1 (i.e. the smallest prime number) by any power, since 1 is lower than 3. Similarly, the first group's size cannot be the result of raising 2 (i.e. the next prime number) in the power of 1, since $2^1=2$ that is also smaller than 3.

However, $2^2=4$ that is not smaller than 3, and the first group of cells is accordingly determined 530 to include four reaction cells.

Further in the calculation of each specific of the cell groups, the group's reaction cells are numbered 0 to k−1, where k is the number of cells in the specific group (i.e. the group's size). Thus, in the example of the group determined 530 to include four cells, the specific group's cells are numbered 0, 1, 2, and 3.

Then, a next one of the groups is calculated 530.

Thus, continuing with the example of the first group that includes four cells, a second group's size is determined 530 by raising the number 3 (i.e. the prime number next to 2) in power 1, since $3^1=3$ that is not smaller than 3. Accordingly, the second group of cells is determined 530 to include three cells, which cells are numbered 0, 1 and 2.

The step of calculating 530 the groups is repeated iteratively, until the product of the sizes of the calculated 530 groups is no smaller than the number of tests raised in the power of the user-input 510 maximal number of concurrently positive tests.

Thus, continuing with the instant example, the calculation is repeated iteratively, until the product of the sizes of the calculated 530 groups is no smaller than $210^2=44,100$.

Accordingly, in the continuing example, a third group of cells is determined to have $5^1=5$ cells and the third group's cells are numbered 0, 1, 2, 3 and 4, a fourth group of cells is determined to have $7^1=7$ cells and the fourth group's cells are numbered 0, 1, 2, 3, 4, 5 and 6. Similarly, a fifth group of cells is determined to have $11^1=11$ cells and the fifth group's cells are numbered 0, 1, 2, 3, 4 . . . 10, and a last and sixth group of cells is determined to have $13^1=13$ cells, and the sixth group's cells are numbered 0, 1, 2, 3, 4 . . . 13.

Indeed, the product of the sizes of the six groups is 4×3×5×7×11×13=60060 that is larger than 44,100, and therefore, the kit of size 43 (i.e. 43 cells) that is the sum of the group's sizes (i.e. 4+3+5+7+11+13) is also big enough for any sub-combination of the kits cells to be indicative of all positive tests and all negative tests, as explained in further detail hereinbelow.

Next, for each one of the tests that the kit is meant to be used for 540, there is calculated 550 the cell number within each one of calculated 530 groups that the test (i.e. the test's reagents) is to be added to. That is to say that each one of the tests is to be added to all cell groups of the kit, by adding the test's reagents to one cell of each group.

For the purpose of that calculation 550, the tests are indexed using natural numbers, staring with 1 (i.e. as $1^{st}$, $2^{nd}$, $3^{rd}$, $4^{th}$ etc.), thus assigning a different index to each test.

In the calculation 550, the number of each group's cell that each specific test is to be added to, is calculated 550 by dividing the index assigned to each one of the tests by the size of the specific group, the reminder being the number of the specific group's cell thus calculated 550—i.e. using a mathematical modulo operation.

Further, the mapping data that maps tests to cells of the kit is updated 560 with data mapping between the test and the cells using the combined group number and cell number data, that each cell is assigned to, using the modulo operation.

Thus, continuing with the instant example, for a test that is indexed $75^{th}$, the cell numbers for the six groups are calculated 550 to be mod (75,4)=3, mod (75,3)=0, mod (75,5)=0, mod (75,7)=5, mod (75,11)=9, and mod (75,13)=10, respectively.

Similarly, for a test that is indexed $150^{th}$, the cell numbers for the six groups are calculated 550 to be 2, 0, 0, 3, 7 and 7, respectively.

When the cells for a specific test are determined 550, the mapping data is updated 560 with data that indicates for each test, all cells that the test is thus mapped to, as described in further detail hereinbelow.

After the cells are determined 550 for all tests 540, the reagents of each specific one of the tests are added 590 to each one of the kit's cells that the mapping data maps the specific test to, say by a robot, as described in further detail hereinbelow.

It is noted that with the second method of distribution, by definition, false positives are not possible, provided the number of concurrently positive test does not exceed the user-input 510 maximum number of tests that can be concurrently positive.

Indeed, continuing with the example, reference is now being made to FIG. 5B, which is a simplified diagram illustrating group size—cell number combinations of a specific example, according to an exemplary embodiment of the present invention.

Going over all size-reminder combinations possible with the example's groups of size 4, 3, 5, 7, 11 and 13, one may calculate the test number that would correspond with each specific size-reminder combination. As illustrated in FIG. 5B, using a table, one can see that only test numbers 75 and 150 are within the 1-210 test number range of the 210 tests of the example. Thus, no other pair of concurrently positive tests is possible with those groups, and accordingly, no false positive resultant upon overlapping with a third test is possible.

Figure 6A:
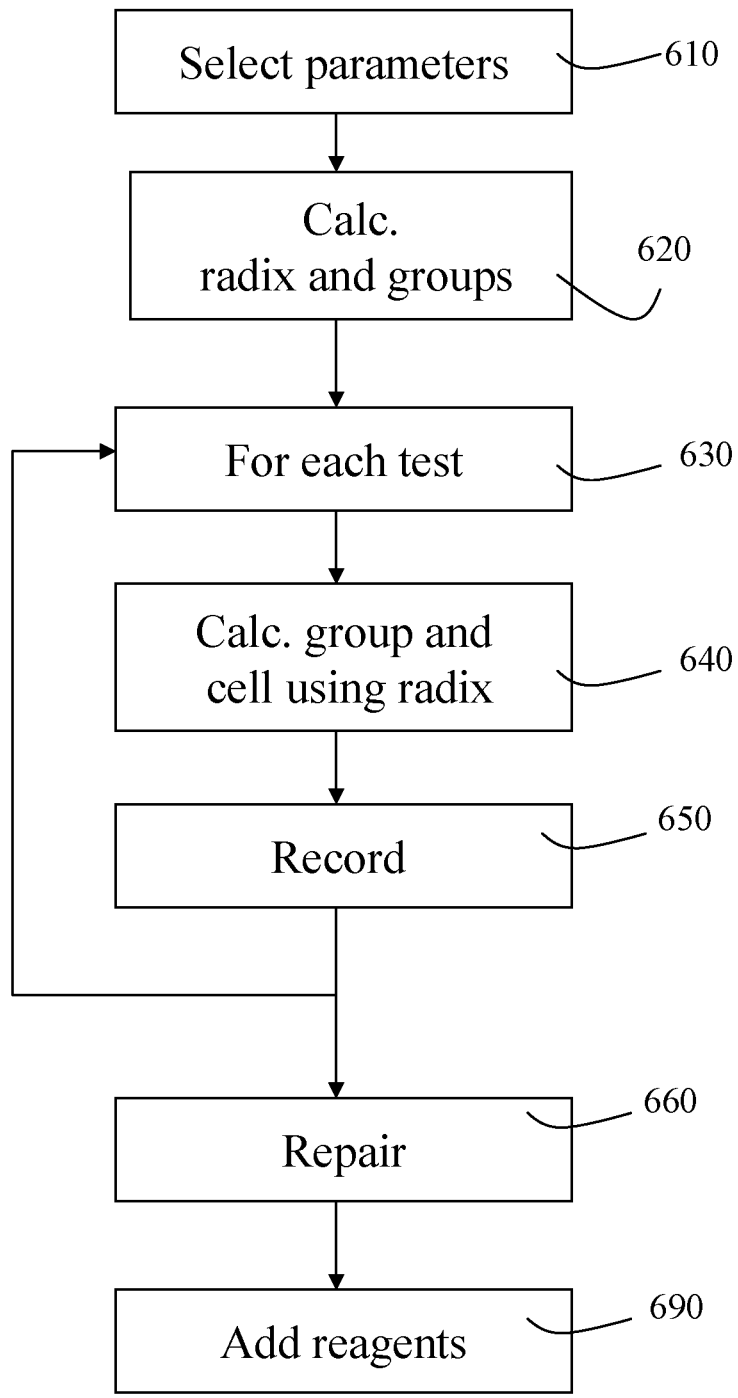
FIG. 6A is a simplified flowchart illustrating a third exemplary method of distributing tests in a multi-test kit, according to an exemplary embodiment of the present invention.

Reference is now made to FIG. 6A, which a simplified flowchart illustrating a third exemplary method of distributing tests in a multi-test kit, according to an exemplary embodiment of the present invention.

A third exemplary method of distributing tests in a multi-test kit, according to an exemplary embodiment of the present invention, may form at least a part of the multi-test kit manufacturing method, as described in further detail hereinabove, and as illustrated using FIG. 1.

The third exemplary distribution method is based on radixes (i.e. on base systems of numeration).

In the third exemplary method of distribution, a user (say a user of a robot a manufacturing robot) is asked (say prompted on a computer screen) to select (i.e. input) 610 the number of tests and the maximum number of tests that can be reliably executed in a same reaction cell (also referred to hereinbelow as the maximum density).

Optionally, the user is also asked to select 610 the maximum number of tests that can be concurrently positive, as described in further detail hereinabove.

Next, two or more cell groups are calculated 620, such that each group includes a same number of cells.

More specifically, for calculating 620 the cell groups, there is selected a radix (also denoted hereinbelow as 'r') and a number of digits positions (denoted hereinbelow as 'd'), so that the number of cells in the kit is at least (r−1)×d and the number of tests is not higher than r^d (i.e. r raised in the power of d), while taking into consideration.

Accordingly, in the calculating 620, there is calculated an array of d groups—i.e. one group per each digit position, such that each group includes (r−1) cells. Accordingly, each group is indexed 1 to d, respectively, and in each one of the groups, each cell is indexed one to (r−1), respectively.

The number of digit positions (d) may be calculated 620 by rounding up the logarithm of the user-input 610 number of tests in the selected 620 radix.

The number of groups is accordingly determined 620 to be the number of digits in the number that is the result of rounding up that logarithm.

Thus, for example, when the radix selected in that calculating 620 is 3, and the user-input 610 maximum number of tests that can be concurrently positive is 2, the number of digit positions (and hence, the number of cell groups) is calculated 620 by deriving the logarithm of the user-input 610 number of tests in base 3.

Thus, in a first example, a user determines 610 (by input) the number of tests that the kit is to be manufactured for, to be 210.

Choosing base (i.e. radix) 3, the number of groups is determined to be 5 that is the result of rounding up the logarithm of 210 in base 3.

Indeed, 210 in base 3 is 21210, which means that five digit positions and thus five groups are required for the kit, such that each group includes two (i.e. r−1=3−1) cells. The total number of cells in the kit is accordingly determined to be ten (i.e. 5×2).

Then, for each one of the tests that the kit is meant to be used for 630, there is calculated 640 the groups and cell number within each one of groups that the test (i.e. the test's reagents) is to be added to.

For the purpose of that calculation 640, the tests are indexed using the natural numbers, staring with 1 (i.e. as $1^{st}$, $2^{nd}$, $3^{rd}$, $4^{th}$ etc.), such that each test is indexed using a different one of the natural numbers between 1 and r^d.

Thus, iterating over all test numbers 630, each test's number is converted in that calculation 640 to the selected 620 radix, and the number that is the result of that conversion, defines which cells of which group the test is to be assigned and distributed to.

More specifically, in the number that is the result of that conversion, each digit's position indicates to which cell of the group that corresponds to that digit position, the test is assigned to. However, if the digit in a specific position is '0', none of the cells of the group that corresponds to digit position occupied by '0' is assigned that test.

Thus, continuing with the first example, for a test indexed as number 75, the test's number when converted to base 3 is 02210, which number defines that test number 75 is assigned to neither one of the cells of the groups that correspond to the digit positions that are first and fifth from the left.

However, the number 02210 also defines that the test is assigned to cell number 2 of the group that corresponds to the second digit position, cell number 2 of the group that corresponds to the third digit position, and call number 1 of the group that corresponds to the fourth digit position.

Similarly, in the first example, for a test indexed as test number 150, the test's number when converted to base 3 is 12120, which number defines that test number 150 is assigned to neither one of the cells of the group that corresponds to the digit position that is fifth from the left.

However, the number 12120 also defines that the test is assigned to cell number 1 of the group that corresponds to the first digit position, cell number 2 of the group that corresponds to the second digit position, cell number 1 of the group that corresponds to the third digit position, and cell number 2 of the group that corresponds to the fourth digit position.

The cells calculated 640 for each test, are then recorded 650 as a part of the mapping data that identifies all the kit's reaction cells that contain an at least one positive test when the test thus mapped to those cells is positive, thus mapping between the kit's tests and cells, as described in further detail hereinabove.

However, a false positive (i.e. a negative test included in the sub-group that includes all positive tests) may still occurs due to an overlap between a sub-combination of the reaction cells that the false positive is mapped to, and combined, sub-combinations of the reaction cells that two or more other tests are mapped to. Optionally, the exemplary method of distribution further includes a step of repairing 660 the recorded 650 mapping data, so as to prevent false positives when up to the user-input 610 number of tests are concurrently positive.

In one exemplary case, in the step of repairing 660, in order to prevent false positives, for the user-input 610 number of concurrently positive tests, there are added control cells to the kit, as described in further detail and illustrated using FIG. 6B-6C hereinbelow.

Finally, the reagents of each specific one of the tests are added 690 to each one of the kit's cells that the mapping data maps the specific test to, say by a robot, as described in further detail hereinabove.

Figure 6B:
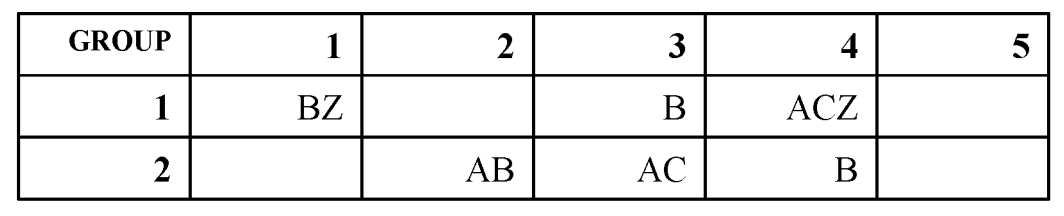

Reference is now made to FIG. 6B, which is a simplified diagram illustrating an exemplary data mapping of tests to cells, based on the third exemplary method of distribution, according to an exemplary embodiment of the present invention.

In one exemplary case, in the step of repairing 660, in order to prevent false positives, for the user-input 610 number of concurrently positive tests, there are added control cells to the kit, as described in further detail and illustrated using FIG. 6B-6C hereinbelow.

The number of control cells added equals to the number of unordered combinations of digit positions (i.e. of cell groups), as described in further detail hereinbelow.

In the exemplary case, if the number of groups (and hence digit positions) is 5, as in the first example, the number of control cells added is 10, since the number of unordered combinations of digit positions is 5×4/2=10, as illustrated in FIG. 6C.

Continuing with the first example, while limiting the illustration to four of the 210 tests of the example, for the sake of simplicity of discussion, the discussion focuses on four of the first example's tests.

In the example, a first test's number is 75 that when converted to base 3, is 02210. Accordingly the first test, that is denoted 'A' in FIG. 6B, is assigned and mapped (using the recorded 650 mapping data) to the second group's second cell, third group's second cell, and fourth group first cell, as illustrated in FIG. 6B.

The first example's second test's number is 150 that when converted to base 3, is 12120. Accordingly the second test, that is denoted 'B' in FIG. 6B, is assigned and mapped (using the recorded 650 mapping data) to the first group's first cell, second group's second cell, third group's first cell, and fourth group second cell, as illustrated in FIG. 6B.

The first example further includes a third test. The third test's number is 21 that when converted to base 3, is 00210. Accordingly the third test, that is denoted 'C' in FIG. 6B, is assigned and mapped (using the recorded 650 mapping data) to the third group's second cell, and to the fourth group first cell, as illustrated in FIG. 6B.

The first example further includes a fourth test. The fourth test's number is 84 that when converted to base 3, is 10010. Accordingly the third test, that is denoted 'Z' in FIG. 6B, is assigned and mapped (using the recorded 650 mapping data) to the first group's first cell, and to the fourth group first cell, as illustrated in FIG. 6B.

As evident from the exemplary mapping data illustrated using FIG. 6B, when Test A is positive, Test C is also included in the sub-group of potentially positive tests, since the recorded 650 mapping data maps Test C to the third group's second cell—that is positive when Test A is positive even if Test C is negative, and to the fourth group first cell—that is also positive when Test A is positive even if Test C is negative. That is to say that when Test A is positive, Test C is a potentially false positive test.

Further, when Tests A and B are positive, Test Z is also included in the sub-group of potentially positive tests, since the recorded 650 mapping data maps Test Z to the first group's first cell—that is positive when Test B is positive even if Test Z is negative, and to the fourth group first cell—that is positive when Test A is positive even if Test Z is negative. That is to say that when both Test A and Test B are positive, Test Z is a potentially false positive.

Reference is now made to FIG. 6C which is a simplified diagram illustrating an exemplary scenario of repairing data mapping of the third exemplary distribution method, according to an exemplary embodiment of the present invention.

In an exemplary scenario of repairing data mapping of the second exemplary distribution method, in order to prevent inclusion of a false positive test in the sub-group of potentially positive tests identified (say in the identifying step 240) using the recorded 650 mapping data, there are added control cells to the kit.

Thus, in the example, the number of groups (and hence digit positions) is 5, and accordingly, the number of control cells added is 10, since the number of unordered combinations of digit positions is 5×4/2=10.

The unordered combinations (1 and 2, 1 and 3, etc.) are illustrated in the second column of the table that is entitled 'Digit Position Group(s)' in FIG. 6C. Accordingly, in the example, one control cell is added per each unordered combination of digit positions.

Then, each test is further assigned to the control cell that corresponds to combination of digit position(s) that the test's number, when converted to the selected 620 radix, has a same digit value (whether '0' or other) in.

Thus, continuing with the first example, Test A has a same digit value ('0') in digit positions 1 and 5 of Test A's number when converted to base 3 (i.e. 02210). Accordingly, Test A is further assigned to the control cell that corresponds to cell groups that correspond to the $1^{st}$ and $5^{th}$ digit positions, i.e. to control cell number 4, as illustrated in FIG. 6C.

Test A also has a same digit value ('2') in digit positions 2 and 3, and is accordingly, further assigned to the control cell that corresponds to cell groups that correspond to the $2^{nd}$ and $3^{rd}$ digit positions, i.e. to control cell number 5, as illustrated in FIG. 6C.

Further in the first example, Test B has a same digit value ('1') in digit positions 1 and 3 of Test B's number when converted to base 3 (i.e. 12120). Accordingly, Test B is further assigned to the control cell that corresponds to cell groups that correspond to the $1^{st}$ and $3^{rd}$ digit positions, i.e. to control cell number 2, as illustrated in FIG. 6C.

Test B also has a same digit value ('2') in digit positions 2 and 4, and is accordingly, further assigned to the control cell that corresponds to cell groups that correspond to the $2^{nd}$ and $4^{th}$ digit positions, i.e. to control cell number 6, as illustrated in FIG. 6C.

Further in the first example, Test C has a same digit value ('0') in digit positions 1 and 2 and is accordingly, further assigned to the control cell that corresponds to cell groups that correspond to the $1^{st}$ and $2^{nd}$ digit positions, i.e. to control cell number 1, as illustrated in FIG. 6C.

However, Test C has that same digit value ('0') in digit positions 1 and 5 too, and is accordingly, further assigned to the control cell that corresponds to cell groups that correspond to the $1^{st}$ and $5^{th}$ digit positions, i.e. to control cell number 4, as illustrated in FIG. 6C.

Test C has that same digit value ('0') in digit positions 2 and 5 too, and is accordingly, further assigned to the control cell that corresponds to cell groups that correspond to the $2^{nd}$ and $5^{th}$ digit positions, i.e. to control cell number 7, as illustrated in FIG. 6C.

Test Z that is numbered 10010 in base 3, is similarly assigned to the control cells that correspond to the $3^{rd}$ and $5^{th}$ digit positions, $2^{nd}$ and $5^{th}$ digit positions, $2^{nd}$ and $3^{rd}$ digit positions, and $1^{st}$ and $4^{th}$ digit positions, i.e. to control cells number 3, 5, 7 and 9.

The recorded mapping data is then updated accordingly, so as to add each test that the test is assigned to, to the list of cells that the test is mapped to using the mapping data. As a result, no false negative is possible.

Thus, for example, the recorded 650 mapping data still maps Test C to the third group's second cell—that is positive when Test A is positive even if Test C is negative, and to the fourth group first cell—that is also positive when Test A is positive even if Test C is negative.

However, Test C is no longer identified as positive when Test A is positive, since the mapping data now maps Test C control cell number 7 too, that does not include an at least one positive test unless Test C itself is positive, and is therefore not positive.

Similarly, when both Test B and Test C are positive, control cell number 5 that Test A is mapped to by the mapping data, is not positive unless Test A itself is positive.

Further, when both Test A and Test C are positive, Test B is no longer identified as positive since for example, according to Test B's mapping by the recorded 650 mapping data, the first group's first cell needs to be positive, and none of Tests A and C is mapped or assigned to the first group's first cell.

Similarly, when both Test A and Test B are positive, Test Z is no longer identified as positive since for example, control cell number 9 that Test Z is mapped to by the mapping data, is not positive unless Test Z itself is positive.

It is expected that during the life of this patent many relevant devices and systems will be developed and the scope of the terms herein, particularly of the terms "Computer" "Robot", "Manufacturing Machine", "Memory", "USB Memory", and "SD Memory", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Further Discussion

A screening test kit for conducting a test for evaluating a specimen for the presence of a large number of chemical compounds using a significantly smaller number of reaction chambers and a limited small set of pre-made chemical mixtures.

The test being predictable regarding the number of different positive detections that can still be accurately distinguishable, and with a predictable statistical specificity when the number of positives is exceeded. All in a single non-adaptive stage of a mass-produced kit. Non adaptive means that the stage composition depends only on the tests being conducted and performance requirements, and not on the internal quantities of the analytes in the specimen.

This should allow a phenomenon to be evaluated for all possible causes that can be tested for in the same kind of a reaction chamber, using a pre-made kit, in a single step.

Definitions for this Further Discussion

Let test be a highly specific test for the presence of a chemical compound, using a chemical process and resulting in a physical measurement.

Let Tests be a large group of such tests each measuring the presence of a different chemical compound of the same type, resulting in a common signal, non-specific to any specific test being positive.

Let Sample be a chemical specimen which we want to evaluate if positive or negative for each one of the tests.

Let Kit be a set of material containers, each container having a unique but overlapping mixture of tests. Each mixture is to be used in its own reaction chamber, where the number of reaction chambers in use is significantly smaller (say magnitude smaller) than the number of Tests that we are conducting to Sample.

In some implementations, a reaction chamber can have a limited number of different sensors, yielding an equal number of 'test channels' that can be used together in the same reaction chamber. For simplicity of language, in this discussion, we refer to each such sensor, channel or chamber, as a different reaction chamber.

Let Separability be the number of simultaneous positive calls that can be made by the kit, with high Specificity.

Let Mixing Procedure be the method by which the different tests are distributed amongst the Kit's containers.

Specific Examples of Chemical Tests that can be Included

Chemical compounds such as specific DNA Sequences, specific proteins, antibodies, toxin traces, explosives traces, etc. Physical measurements can be fluorescence intensity, phosphorescence, electric conductivity, electric capacitance, optical opacity of regions of the reaction chamber, etc. Reaction chambers can be test tubes in a fluorescence detecting Thermal Cycler, test tubes in an isothermal device with phosphorescence detection, wells used for blotting in ELISA tests, etc., as known in the art.

Exemplary Methods

Designing the Kit

Let N be the number of different target compounds for which we are testing a sample.

Let D Be the Separability, the maximum number of simultaneous positive results that our Kit is set to distinguish among.

Let T be the number of unique test mixes in our kit to be placed in T reaction chambers.

A mixing procedure is chosen that optimizes between:
1. Satisfying requirements of factor D
2. Not placing together in the same mix, tests which are known to interfere with each other, or are known to be likely positive at the same time.
3. Optimizing the value T to engineering requirements: for example, how many reaction chambers fit in an analysis instrument for a single batch.
4. As uniform as possible distribution of test variants between the T mixes.
5. Minimize the number of different tests for each mix, to reduce manufacturing steps and test load in a single well.

The parameters of the mixing procedure, such as 'subgroup-size' or 'number-of-mixes' or 'radix', are further optimized to overcome technical limitations and match the design requirements. Such a choice can be made, for example, by using an exhaustive search for all combinations of parameters, linear programming, Newton-Gauss Minimization or any other technique fit for purpose, to choose a passable or ideal combination of design parameters.

A decision is made regarding the value of T as a function of D and N, and the chosen Mixing Procedure in use for construction of the Kit.

Place each test in appropriate group of multiple different mixes, group being a subsection of the T mixes.

A subsection of the T mixes can optionally be used for error correction purposes, for the ability to resolve result conflicts to achieve the requirement of D separable simultaneous positive answers.

Example of some mixes and tests is given in the following Assignment Table:

| Test | 1 | 2 | 3 | 4 | 5 | 6 | 7 | 8 | 9 | 10 | 11 | 12 |
|---|---|---|---|---|---|---|---|---|---|---|---|---|
| Mix | D | A, B | | C, B | A | B | D | | A, C | D | B | C |

Optionally scan possible permutations of simultaneous positive calls for the tests, to identify where a combination of positive tests can yield a positive reaction chamber pattern that obscures other tests that may be simultaneously positive. In such case, use allocated control reaction chambers (say wells), having found obscured tests to allow accurate detection if these are obscured by other positive tests.

The following exemplary assignment tables resolve 2 positives:

| MIX | Chamber | Test A | Test B | Test C | Test D | ... | Test Z |
|---|---|---|---|---|---|---|---|
| 1 | A1 | | | | X | | X |
| 2 | A2 | X | X | | | | |
| 3 | A3 | | | | | | |
| 4 | A4 | | X | X | | | |
| 5 | B1 | X | | | | | X |
| 6 | B2 | | | | | | |
| 7 | B3 | | | | X | | X |
| 8 | B4 | | | | | | |
| 9 | C1 | X | | X | | | |
| 10 | C2 | | | | X | | |
| 11 | C3 | | X | | | | |
| 12 | C4 | | | X | | | |
| Ctrl | D1 | X | X | | X | | |

| D1, Z1 | A2, B2 | B4, C4 | A5, Z5 | D7, Z7 | A9, C9 | Total: |
|---|---|---|---|---|---|---|
| D | A | B | A | D | A | A, B, D |

A single collision is possible, if test shares mixes, and it's index is lower than colliding test.

Record a lookup table between each test, and the mixes in which it appears. In which mixes, each test appears.

Using the Kit

When conducting the test, distribute a representative subsection of the Sample, into each of the reaction chambers used for the test. When the chemical process is complete, read which of the reaction chambers yields a positive signal. If no positive signal is read, then there are no tests which are positive.

Example of assigning mixes to reaction chambers is given in the following table:

| Test | 1 | 2 | 3 | 4 | 5 | 6 | 7 | 8 | 9 | 10 | 11 | 12 |
|---|---|---|---|---|---|---|---|---|---|---|---|---|
| Mix | D | A, B | | C, B | A | B | D | | A, C | D | B | C |
| Chamber | A1 | A2 | A3 | A4 | B1 | B2 | B3 | B4 | C1 | C2 | C3 | C4 |

Otherwise, iterate through the dictionary of tests and their mix placements, and list tests for which all mix placements show a positive signal.

Example of a dictionary (also referred to as a look-up table or a reference table):

| MIX | 1 | 2 | 3 | 4 | 5 | 6 | 7 | 8 | 9 | 10 | 11 | 12 |
|---|---|---|---|---|---|---|---|---|---|---|---|---|
| Chamber | A1 | A2 | A3 | A4 | B1 | B2 | B3 | B4 | C1 | C2 | C3 | C4 |
| Test A |  | X |  | X |  |  |  |  | X |  |  |  |
| Test B |  | X |  | X |  |  |  |  |  |  | X |  |
| Test C |  |  |  | X |  |  |  |  |  | X |  | X |
| Test D | X |  |  |  |  | X |  |  |  | X |  |  |
| ... |  |  |  |  |  |  |  |  |  |  |  |  |
| Test Z | X |  |  |  | X | X |  |  |  |  |  |  |

An alternative to having a dictionary of patterns of tests, would be to have the pattern of reaction chambers itself, represent a numerical value, for example, using a radix system as described in further detail hereinbelow.

If all mixes having a certain test are positive, then this test is a candidate from being positive.

If only one test is a candidate for being positive, then this test is positive.

Thus, in one exemplary method:
 Read lookup table of mix placements per test
 Loop until all tests have iterated:
  Take next test
  Take list of mixes having test
  Collect results of all reaction chambers having mixes having test.
  Are all results collected positive?
   List test as suspected positive
 If tests are quantitative, and more than one quantity is measured, assign quantities to tests using a linear system on the suspected positive combination placements.
 Calculate false positive probability as a function of the number of positives, the number of different mixes, and the number of repeated placements.
 Send results and probabilities Example of decoding when a single test is positive:

| Chambers | Mixes | Match Test |
|---|---|---|
| A2, A4, C3 | 2, 4, 11 | Test B |

If more than one test is a candidate for being positive, but there is only one way to resolve which positive tests would generate that certain mix pattern, then these tests are positive.

If the patterns of mix placements of tests are randomly distributed, and the count of mix placements for each test is equal, then we can always know when there is more than one positive tests in our test.

If there is more than one test that is a candidate for being positive, and more than one possible solution to which tests are, alert operator for probability of a false positive for each result.

Multiple solutions are possible due to intersections of multiple positive tests patterns that may obscure a positive test behind their union. The probability of such a false positive occurring, (not taking into account domain specific limitations), is a function of T (number of reaction chambers), the number of test channels (say color sensors) in use, and N (number of tests), and can be reported to the operator.

For a sufficiently large value of T, the asymptotic probability is for a false positive is 1/n, as known in the art.

Optionally, given a test that is featuring relative quantification, it is possible to evaluate the quantity of Sample responsive to a test, in a given mix. Results of the same test, are expected to have the same relative Quantity across reaction chambers, given that the Sample distribution between the reaction chambers is uniform. In such case, apply a quantity condition for filtering through possible test-combination solutions for the reaction chambers positivist pattern.

Thus, in one exemplary method:
 Read lookup of mix placements per test
 Let t be the index over the tests group T. Let m be an index over the Mixes group M
 Read the total quantity of each reaction chamber.
 List all tests which may be positive, given test placement.
 Create a general m×n linear system, where n is the number of tests and m is the number of mixes, for example:

$$a_{11}x_1 + a_{12}x_2 + \ldots + a_{1n}x_n = b_1$$
$$a_{21}x_1 + a_{22}x_2 + \ldots + a_{1n}x_n = b_2$$
$$a_{31}x_1 + a_{32}x_2 + \ldots + a_{1n}x_n = b_3$$
$$\vdots$$
$$a_{m1}x_1 + a_{m2}x_2 + \ldots + a_{mn}x_n = b_m$$

Let the system coefficients ai,j be 1 if test of index i exists in mix index j, AND test of index i is a candidate for being positive. Otherwise, 0
 Let the system constants bj be the shared quantity readout of the reaction chamber having mix index j
 If the number of tests candidates to being positive, is smaller or equal to the number of equations whose coefficients for these tests are non-zero, then the system is solvable
 Is system solvable?
  Use a linear system solver
  If system is solvable, the solution would be the relative quantity all results collected positive of each candidate test.
  Report quantities and residual errors to operators
 Otherwise, Report ambiguities as unresolvable A relative quantity is measures with respect to either a standard quantity or any other quantity in question. For the same object we're measuring, we can have another 'absolute' measurement that is irrespective of other objects.

In here, in the example below, the absolute unknown quantity is the concentration of target material in a given reaction chamber. While this cannot always be inferred, the ratio between the absolute quantities of target material in two different chambers, can be inferred by converting the measured signal to units having a linear relation to quantity. When this is done, the ratio between two such measurement of two chambers (in units linearly related to quantity), will be equal to the ratio between absolute quantities. This is based on the assumption that, within the same plate, the unknown factor between linear units and absolute quantity, is consistent across different chambers.

Example of decoding multiple positives in given in the following table:
All Possible Matches

| MIX | 1 | 2 | 3 | 4 | 5 | 6 | 7 | 8 | 9 | 10 | 11 | 12 |
|---|---|---|---|---|---|---|---|---|---|---|---|---|
| Chamber | A1 | A2 | A3 | A4 | B1 | B2 | B3 | B4 | C1 | C2 | C3 | C4 |
| Test A |  | X |  |  | X |  |  |  | X |  |  |  |
| Test B |  | X |  | X |  |  |  |  |  |  | X |  |
| Test C |  |  |  | X |  |  |  |  | X |  |  | X |
| Test D | X |  |  |  |  |  | X |  |  | X |  |  |
| ... |  |  |  |  |  |  |  |  |  |  |  |  |
| Test Z | X |  |  |  |  | X | X |  |  |  |  |  |

The possible Solutions: Tests A, B, D, Z are positive; Tests A, B, D are positive—i.e. we are unsure if Z is an actual positive.

Placement table example of solving such ambiguities by quantifying.

The following able is the linear unit relative quantity, which is the result of analyzing the plate setup listed immediately hereinabove. For example, Mix 5 in chamber B1, has a value of 2, due to a contribution of Test A and Test Z.

| MIX | 1 | 2 | 3 | 4 | 5 | 6 | 7 | 8 | 9 | 10 | 11 | 12 |
|---|---|---|---|---|---|---|---|---|---|---|---|---|
| Chamber | A1 | A2 | A3 | A4 | B1 | B2 | B3 | B4 | C1 | C2 | C3 | C4 |
| Relative Quantity | 3 | 4 |  | 3 | 2 |  | 3 |  | 1 | 2 | 3 |  |

The table below is a linear equation system.

The unknowns are the relative quantities of each test A to Z. (Column Test, Test). Each Row corresponds to a different MIX in a chamber. The unknowns in each row represent tests of the Mix represented in the Row. Relative quantity is the total physical readout of a in linear units of the Row's chamber.

The linear system in the table below, has a Single solution mapping the following relative quantities to the following tests: A=1, B=3, D=2, Z=1

| Mix | Test |   | Test |   | Relative quantity |
|---|---|---|---|---|---|
| 1 | D | + | Z= |  | 3 |
| 2 | A | + | B= |  | 4 |
| 4 | B |   | =  |  | 3 |
| 5 | A | + | Z= |  | 2 |
| 7 | D | + | Z= |  | 3 |
| 9 | A |   | =  |  | 1 |
| 10 | D |   | = |  | 2 |
| 11 | B |   | = |  | 3 |

Practical Examples for Strategies
Specific Strategies for distribution of tests among the mixes Definition for the Following Separability: How many simultaneous positives the kit can classify reliably.

Maximum density: The number of tests that can be reliably be executed simultaneously in a single mix. This can take into account reaction volume, the tests competing for reagents, etc.

Random Strategy
In this strategy, a total amount of total mixes, and an amount of different mixes amongst which each test will be distributed, are selected to satisfy a low probability for false positive readings for the expected number of simultaneous positives.

The probability can be combinatorially calculated, given the amount of possible permutations, and the likelihood of a combination yielding a false positive occurring.

For example, having 96 mixes, where each test is randomly distributed amongst 8 mixes, and we have 1024 different tests amongst which we expect at most 2 tests to be positive simultaneously, then the probability of a mistaken readout, say by two tests forming the positivity pattern of a 3rd test, is less than 0.001.

In one exemplary method:
    Optimize mix count and repeat placement count
    Loop until all tests have been iterated
        Take next test from test group
        Was count fulfilled for test?
            Let Index be a random number between 1 and number of mixes
            Put test in Mix of Index
            Record in dictionary mix index for test
    Manufacture Kit Practical Kit Optimization Strategy for Random Strategy
    We expect at most d concurrent positives.
    We wish to test n unique tests.
    Let m be the maximum density of tests allowed in one tube (the most tests that can simultaneously function in one mix).
    The number of mixes t required is at least
    $2 \cdot \log n + 4 \cdot d \cdot \log(e \cdot n/d)$ rounded up to the next multiple of d.
    Each test will be randomly placed into $t/2 \cdot d$ different mixes. The placement map of each mix is stored in a lookup.
    At this stage, the probability of mistaken positive happening due to a random pattern combination of 2 other positive is 2 raised in the power of $(-t/2d)$, due to the need for two random patterns to match.
    To alleviate any chance of mistake, iterate through all possible combinations of d concurrent positives. If a combination reveals a possibility of a pattern from the lookup completely obscured by the concurrent positives pattern, change the obscured pattern, and repeat the process until there are no more obstructions.

A Numerical Example

Suppose we want to distinguish between the results of 210 different tests.

Suppose we expect at most 2 simultaneous positives.
To calculate the number of mixes:
$2 \cdot \log 210 + 4 \cdot 2 \cdot \log(e \cdot 210/2)$ rounded to next multiple of d gives 24 mixes.

The number of mixes, each test is placed onto is $24/2 \cdot 2 = 6$.

Let's take tests AB CD as an example, and, although the low probability, simulate and obstruction.
    Test A Random Mixes: 16, 4, 24, 6, 3, 10.
    Test B Random Mixes: 1, 10, 15, 2, 13, 11.
    Test C Random Mixes: 23, 5, 10, 18, 17, 14.
    Test D mixes: 2, 18, 13, 14, 17, 11 (simulated to cause an obscuration).
    All possible 2-positive combinations of that set:
    A+B→16, 4, 24, 6, 3, 10, 1, 15, 2, 13, 11
    A+C→16, 4, 24, 6, 3, 10, 23, 5, 18, 17, 14
    A+D→16, 4, 24, 6, 3, 10, 2, 18, 13, 14, 17
    B+C→1, 15, 2, 13, 11, 23, 5, 10, 18, 17, 14
    B+D→1, 10, 15, 2, 13, 11, 18, 14, 17
    C+D→23, 5, 10, 18, 17, 14, 2, 13, 14, 11

31

It is visible to see that pattern B+C would cause the detection of pattern D
B+C→1, 15, 2, 13, 11, 23, 5, 10, 18, 17, 14
D=2, 18, 13, 14, 17, 11

Any shuffling of test D placements, is likely to remove the problem with a very high probability of success, and can be repeated if it does not resolve the obscuration.

D*=16, 13, 2, 14, 20, 24 (Random selection of mixes for test D) no longer creates an obscuration on any 2-positive combinations in this set.

Alternatively, to avoid rescanning for duplicates, it is possible to use an extra mix, where any test found to be obscured can be placed, making it non-observable.

The reason is that an extra mix will not obscure current existing test patterns, and will not be obscured by existing test patterns.

These strategies for obscuration correction are applicable to any one of the following construction strategies too.

Powers of Primes Strategy

Natural Number: 1, 2, 3 . . . infinity.

In this strategy, the test group is assigned an incremental index.

A group of natural powers of unique prime numbers is constructed.

The group of primes is selected, so that their multiple at least the number of tests, raised by the power of the required Separability factor. The group is optimized so the sum of the prime powers, is as small as possible, to achieve results in as fewer tests, considering technical limitations. As a test would appear in all mix-groups (defined below), we may raise the power of the prime, or choose a larger prime, to avoid having too many tests in one mix, which may raise a technical limitation regarding the maximal test capacity of a mix.

For each natural power of prime, make a new mix group, having (at least) as many mixes as the value of that power of prime. Index the mixes incrementally.

For each test in the test group, place the test in each mix in the mix group, if the index of that mix, when divided by the natural power of prime, has the same reminder, as the index of the test, when divided by the natural power of prime.

Add the new mix group to the kit collection, and repeat for with the next natural power of prime from the group.

Practical Kit Optimization Strategy for Powers of Primes.

We expect at most d concurrent positives. We wish to test n unique tests.

Given that each test exists in each group of a power of prime, the smallest number of mixes for a group is n/d.

Select a prime number, raise in power so that the result is at least n/d

Repeat with next prime numbers raised to whole powers so that each result is at least n/d, until the multiplication of all values calculated by raising the prime numbers in the powers in the previous steps, is at least n to the power of d.

In each group of mixes belonging to a whole power of prime, place a test into a mix if the reminder of the division of the index of that test, by the power of prime of the mix group, equals to the index of the mix inside the mix group.

Repeat for all tests.

Using known prime number density theory, the theoretical lower bound for the number of mixes is: $d^2 \log^2 n/(\log d + \log \log n)$.

Thus, in one exemplary method:
Optimize size of pool of whole powers of unique primes and number of mixes
Assign incremental index to the group of tests T

32

Loop until all power of primes have iterated
  Take next i power of prime p as pi from the pool
  Assign pi mixes to a new group M having an incremental index
  Loop until all combinations are iterated
    Take next unique unordered combination of test from T and mix from M having indexes t and m respectively
    If the remainder of an integer division oft by pe equals to m, assign test T[t] to Mix M[m]
Manufacture Kit fulfilling all test to mix placements.

A Numerical Example

Note: In this example, small numbers are used for ease of explanation.

Suppose we can put at most 70 tests in the same mix, we want to distinguish 210 different tests, and Suppose we expect at most 2 simultaneous positives.

Therefore, we know that Smallest size of a group is 210/70=3, and accordingly, the multiplying of all mix group sizes should yield at least $210^2$=44100.

Group #1 is of prime 2. Power 1 will set a group size below the limit. Power 2 will set a group size of 4, which is sufficient.

Group #2 is of prime 3, which is large enough having power 1.

Group #3 is of prime 5, which is large enough having power 1.

Group #4 is of prime 7, which is large enough having power 1.

Group #5 is of prime 11, which is large enough having power 1.

Group #6 is of prime 13, which is large enough having power 1.

Multiplying group sizes: 2²·3·5·7·11·13=60060 which is larger than 210 in the power of 2. Therefore 43 mixes are sufficient to evaluate 210 tests having at most 2 simultaneous positives.

Let's take tests having index 75 and test 150.

As these share a common reminder with some of the group sizes, they will partially obscure each other.

Their indexes for each group size are: mod(75, 4)=3; mod(75, 3)=0; mod(75, 5)=0; mod(75, 7)=5; mod(75, 11)=9; mod(75,13)=10.

So 75 maps to {3}, {0}, {0}, {5}, {9}, {10} and similarly, 150 maps to {2}, {0}, {0}, {3}, {7}, {7}.

If test results are positive simultaneously, we will get the reaction chamber pattern (note: multiple indexes in same group are marked as a collection within):

{2, 3}, {0}, {0}, {3,5}, {7,9}, {7,10}

Addressing the lookup table, both #75 and #150 are detected.

Is it possible that another positive figure will be falsely detected? We'll take a reminder pattern different from that of #75 and #150, and see if it can account for an index within our test range of 210.

The possible combinations and the smallest natural numbers matching the reminder patterns are shown in the following table:

| Group: | 4 | 3 | 5 | 7 | 11 | 13 | Result |
|---|---|---|---|---|---|---|---|
| Reminder | 2 | 0 | 0 | 3 | 9 | 10 | 23670 |
|  | 2 | 0 | 0 | 3 | 9 | 7 | 32910 |
|  | 2 | 0 | 0 | 3 | 7 | 10 | 50970 |

-continued

| Group: | 4 | 3 | 5 | 7 | 11 | 13 | Result |
|---|---|---|---|---|---|---|---|
| | 2 | 0 | 0 | 3 | 7 | 7 | 150 |
| | 2 | 0 | 0 | 5 | 9 | 10 | 15090 |
| | 2 | 0 | 0 | 5 | 9 | 7 | 24330 |
| | 2 | 0 | 0 | 5 | 7 | 10 | 42390 |
| | 2 | 0 | 0 | 5 | 7 | 7 | 51630 |
| | 3 | 0 | 0 | 3 | 9 | 10 | 8655 |
| | 3 | 0 | 0 | 3 | 9 | 7 | 17895 |
| | 3 | 0 | 0 | 3 | 7 | 10 | 35955 |
| | 3 | 0 | 0 | 3 | 7 | 7 | 45195 |
| | 3 | 0 | 0 | 5 | 9 | 10 | 75 |
| | 3 | 0 | 0 | 5 | 9 | 7 | 9315 |
| | 3 | 0 | 0 | 5 | 7 | 10 | 27375 |
| | 3 | 0 | 0 | 5 | 7 | 7 | 36615 |

As visible from this table, the only 2 combinations that have an index within the possible test range, are the correct calls of 75 and 150.

Radix Strategy

A 'radix' value is selected, and a digit value is selected, so that the number of mixes is at least $(r-1) \cdot d$ and the number of tests is at most r raised in the power of d rd, considering technical limitations.

A unique natural number is assigned to each test in test group, between 1 and r raised in the power of d.

Create an array of d groups of $r-1$ mixes each, each group indexed, each mix indexed in that group.

For each test, as represented by its assigned number, in radix r:
  For each non-zero digit of the integer representation of the assign number, having placement index p and value:
    Place the test in a mix in mix group having index p, where the internal index of the mix in the group is v.

Practical kit optimization strategy for radix strategy:

Radix 3+Control mixes is a useful combination for 2-simultanious-positives.

Suppose we want to distinguish N different tests:
    The number of digit groups G required is $\log_3(N)$ rounded to next integer
    Each group have 2 wells, one for each non-zero possible digit value of a test index
      Note: Digit 0 (or any single specific digit) can be omitted as a default value.
    Convert index values to base 3
    Place a test in a mix, if the digit-group index of the mix and the digit-value represented by the index of the mix within the digit-group, is the same as the value at the digit position of the base-3 index value of the test index.
  To distinguish between 2-simultaneous positives:
    Allocate number of combinations of 2 items from G (digit groups) items.
    Each mix corresponds to a unique unordered combination of different digit group indexes.
    Please a test in a mix, if both digit groups in the combination referenced by the mix, have the same digit value for that test (0, 1 or 2).

Note: This adds extra mixes to our tests in proportion to the number of occlusions that can occur. It also allows calculating the index of the test without a lookup table, where ambiguities are resolved by the knowledge stored in the control, that a specific previous index had an identical value for the reviewed test.

Thus, in one exemplary method:
  Optimize radix r and an integer d, so that the number of mixes is at least $(r-1) \cdot d$ and the number of tests is at most (r in the power of d)−1

For each test, assign a different integer between 1 and (r in the power of d)−1 and record integer to test mapping
  Create D, an array of d groups of $r-1$ mixes each, each group indexed from 0 to d−1 each mix indexed in that group from 1 to $r-1$
  Take next test t from test pool. Let i be the integer associated with it.
  Loop until all tests have iterated
    Loop until all non-zero digits iterated
      For next non-zero digit of the number i, let p be the position of that digit between 0 and d−1, and v the value of that digit, between 1 and $r-1$
      Assign test t to mix v in mix-group having index p of array D
  Manufacture Kit fulfilling all test to mix placements.

A Numerical Example

Suppose we want to distinguish 210 different tests.
We'll use Radix 3, while adding a mix.
The number of digit groups required is log in base 2 of 210, rounded to next integer=5.
To elaborate, 210 in base 3 is 21210, which means that 5-digit groups are required, each having 2 mixes, which amounts to 10 mixes.
To the number of mixes required for 1 simultaneous detection is 2(base)·5(digits)=10.
In case of having multiple simultaneous tests as positives, we will see multiple chambers as positive in at least one-digit group.
To make a test allowing for 2 simultaneous positive calls, we can add an extra control mix, for each unordered combination of digit group, every mix for a total of 20 mixes (because there are 10 combinations of 2 items from 5 items).
For every two-digit position in a test pattern, having the same value, place the test in the control well associated with that position combination. This condition is chosen as example, as any similar structural property may do. Naturally, there is no need to include empty mixes in our manufactured test.
Take test A=#75 and test B=#150. In base 3: A=02210, B=12120. To make an example, we'll use a test index C which intentionally might be obscured by B and A. C=#21, which is in Base 3: 00210. Thus, in a test mix composition table:

| Digit Group | 1 | 2 | 3 | 4 | 5 |
|---|---|---|---|---|---|
| 0 | | | | | |
| 1 | B | | B | AC | |
| 2 | | AB | AC | B | |

Controls (Adds wells to correspond with an arbitrary structure property) table:

| Control | Digit groups | Tests where digit groups have same value | Elaboration |
|---|---|---|---|
| 1 | 1, 2 | C | 00210 in base 3 |
| 2 | 1, 3 | B | 12120 in base 3 |
| 3 | 1, 4 | | |
| 4 | 1, 5 | A, C | 02210 in base 3, 00210 in base 3 |
| 5 | 2, 3 | A | 02210 in base 3 |
| 6 | 2, 4 | B | 12120 in base 3 |
| 7 | 2, 5 | C | 00210 in base 3 |

-continued

| Control | Digit groups | Tests where digit groups have same value | Elaboration |
|---|---|---|---|
| 8 | 3, 4 | | |
| 9 | 3, 5 | | |
| 10 | 4, 5 | | |

Explanation: B has the same value 1 for digit positions 1 and 3. B has the same value 2 for positions 2 and 4. A has the same value 0 for digit positions 1 and 5 and so on. Two-simultaneous positive combinations are shown in the following tables:

| A + B | | | | | |
|---|---|---|---|---|---|
| Digit Group | 1 | 2 | 3 | 4 | 5 |
| 1 | X | | X | X | |
| 2 | | X | X | X | |
| Controls 1-5 | | X | | X | X |
| Controls 6-10 | X | | | | |

As evident, Control Mix #7 is not positive, which means C is not present (as it lacks that reaction chamber showing a positive reaction for test C).

| B + C | | | | | |
|---|---|---|---|---|---|
| Digit Group | 1 | 2 | 3 | 4 | 5 |
| 1 | X | | X | X | |
| 2 | | X | X | X | |
| Controls 1-5 | X | X | | X | |
| Controls 6-10 | X | X | | | |

As evident, Control Mix #5 that is part of pattern A, doesn't react in the reaction chamber, so the combination is only B+C

| A + C | | | | | |
|---|---|---|---|---|---|
| Digit Group | 1 | 2 | 3 | 4 | 5 |
| 1 | | | | X | |
| 2 | | X | X | | |
| Control 1 | X | | | X | X |
| Control 2 | | X | | | |

This shows the reaction chambers of the pattern of A and the pattern of C as positive. B is missing some of its pattern, so isn't present.

What is claimed is:

1. A prefabricated multi-test kit, the kit comprising:
a plurality of reaction cells, each one of at least two of said reaction cells holding a respective, different set of at least two tests selected from a group consisting of a plurality of different tests,
the tests of the group being distributed among the reaction cells in a manner that leaves each different one of the tests of the group in each reaction cell of a respective different sub-combination of said reaction cells, and allows any sub-combination of said reaction cells to be indicative of a sub-group comprising all positive tests of the group when each reaction cell of the sub-combination that is indicative of the sub-group, contains an at least one positive test and none of the remaining reaction cells contain a positive test, such that the reaction cells are fewer than the tests being distributed among the reaction cells, the distributed tests thereby being condensed into the fewer reaction cells while still allowing the sub-combination to be indicative of the sub-group when each reaction cell of the sub-combination that is indicative of the sub-group contains an at least one positive test and none of the remaining reaction cells contain a positive test.

2. The kit of claim 1, wherein the manner of distribution of said tests among the reaction cells further allows the sub-combination of said reaction cells to be indicative of all negative tests of the group.

3. The kit of claim 1, wherein the manner of distribution of said tests among the reaction cells further allows the sub-combination of said reaction cells to be indicative of all negative tests of the group, provided the number of concurrently positive tests is below a predefined number.

4. The kit of claim 1, wherein the manner of distribution of said tests among the reaction cells further allows the sub-combination of said reaction cells to be indicative of all negative tests of the group, within a predefined degree of certainty.

5. The kit of claim 1, further comprising a plurality of sensors, each one of the sensors being configured to measure a value of a physical property over a respective one of the reaction cells.

6. The kit of claim 5, further comprising a computer in communication with said sensors.

7. The kit of claim 5, further comprising a computer in communication with said sensors, configured to determine for each respective one of the reaction cells, whether the cell holds at least one positive test, based on the value of the physical property measured over the reaction cell.

8. The kit of claim 1, further comprising an at least partially physical interface that is connectable to an external computer, for allowing the external computer to read the physical property values measured by said sensors.

9. A method of manufacturing a multi-test kit, the method comprising:
providing a plurality of reaction cells; and
distributing a group consisting of a plurality of tests among the reaction cells, by adding each different one of the tests of the group to each reaction cell of a respective different sub-combination of the reaction cells and leaving a set of at least two of the tests of the group in each respective one of at least two of the reaction cells, in a manner that allows any sub-combination of the reaction cells to be indicative of a sub-group comprising all positive ones of the tests of the group when each reaction cell of the sub-combination that is indicative of the sub-group, contains at least one positive test and none of the remaining ones of the reaction cells contain a positive test, such that the reaction cells are fewer than the tests being distributed among the reaction cells, the distributed tests thereby being condensed into the fewer reaction cells while still allowing the sub-combination to be indicative of the sub-group when each reaction cell of the sub-combination that is indicative of the sub-group contains an at least one positive test and none of the remaining reaction cells contain a positive test.

10. The method of claim 9, wherein the manner of distribution of the tests among the provided reaction cells further allows the sub-combination of the reaction cells to be indicative of all negative tests of the group.

11. The method of claim 9, wherein the manner of distribution of the tests among the provided reaction cells further allows the sub-combination of the reaction cells to be indicative of all negative tests of the group, provided the number of concurrently positive tests is below a predefined number.

12. The method of claim 9, wherein the manner of distribution of the tests among the provided reaction cells further allows the sub-combination of the reaction cells to be indicative of all negative tests of the group, within a predefined degree of certainty.

13. The method of claim 9, further comprising providing data mapping between each one of the different tests of the group and a respective sub-combination of the provided reaction cells, the mapping identifying all reaction cells that contain an at least one positive test when the test mapped to the sub-combination is positive.

14. A method of carrying out a plurality of tests using a multi-test kit, the method comprising:
receiving data identifying for each respective one of the plurality of tests, all reaction cells of the multi-test kit that contain an at least one positive test when the respective one of the plurality of tests is positive;
dividing a sample among a plurality of reaction cells of the multi-test kit,
each one of at least two of the reaction cells of the kit holding a respective, different set of at least two tests selected from the plurality of tests, the tests being distributed among the reaction cells in a manner that leaves each different test of the plurality of tests in each reaction cell of a respective different sub-combination of the reaction cells, and allows any sub-combination of the reaction cells to be indicative of a sub-group comprising all positive tests of the plurality of tests when each reaction cell of the sub-combination that is indicative of the sub-group, contains an at least one positive test and none of the remaining reaction cells contain a positive test, such that the reaction cells are fewer than the tests being distributed among the reaction cells, the distributed tests thereby being condensed into the fewer reaction cells while still allowing the sub-combination to be indicative of the sub-group when each reaction cell of the sub-combination that is indicative of the sub-group contains an at least one positive test and none of the remaining reaction cells contain a positive test;
measuring a physical property over each cell of the reaction cells of the kit that holds at least one of the tests;
for each one of the reaction cells of the kit that holds at least one of the tests, determining whether the reaction cell contains an at least one positive test, based on said measuring; and
based on said determining and using the received data, identifying a subgroup comprising all positive tests of the plurality of tests.

15. The method of claim 14, wherein the manner of distribution of the tests among the reaction cells further allows the sub-combination of the reaction cells to be indicative of all negative tests of the plurality of tests, the method further comprising identifying all negative tests of the plurality of tests, based on said determining and using the received data.

16. The method of claim 14, wherein the manner of distribution of the tests among the reaction cells further allows the sub-combination of the reaction cells to be indicative of all negative tests of the plurality of tests, provided the number of concurrently positive tests is below a predefined number, the method further comprising identifying all negative tests of the plurality of tests, based on said determining and using the received data, provided the number of concurrently positive tests is below the predefined number.

17. The method of claim 14, wherein the manner of distribution of the tests among the reaction cells further allows the sub-combination of the reaction cells to be indicative of all negative tests of the plurality of tests, within a predefined degree of certainty, the method further comprising identifying all negative tests of the plurality of tests, within the predefined degree of certainty, based on said determining and using the received data.

* * * * *